United States Patent
Robertson et al.

(10) Patent No.: US 6,709,866 B2
(45) Date of Patent: Mar. 23, 2004

(54) METHODS FOR ENHANCING SURVIVAL OF A NEURON

(75) Inventors: George S. Robertson, Ottawa (CA); Robert G. Korneluk, Ottawa (CA); Alexander E. MacKenzie, Ottawa (CA); Daigen Xu, Ottawa (CA); Stephen J. Crocker, Halifax, CA (US)

(73) Assignee: Aegera Therapeutics, Inc., Verdun (CA)

( * ) Notice: Subject to any disclaimer, the term of this patent is extended or adjusted under 35 U.S.C. 154(b) by 273 days.

(21) Appl. No.: 09/735,066

(22) Filed: Dec. 11, 2000

(65) Prior Publication Data

US 2001/0021699 A1 Sep. 13, 2001

Related U.S. Application Data

(63) Continuation of application No. 08/844,693, filed on Apr. 25, 1997, now Pat. No. 6,159,948.
(60) Provisional application No. 60/030,590, filed on Nov. 14, 1996, and provisional application No. 60/017,354, filed on Apr. 26, 1996.

(51) Int. Cl.$^7$ .................. C12N 15/63; C12N 15/00; C12N 15/85; C12N 15/86; C12N 15/74
(52) U.S. Cl. .................. 435/455; 435/4; 435/6; 435/375; 435/440; 435/456; 435/476
(58) Field of Search .................. 435/325, 455, 435/456, 476

(56) References Cited

U.S. PATENT DOCUMENTS 6,187,557 B1   2/2001   Rothe et al. .............. 435/69.1

FOREIGN PATENT DOCUMENTS

| WO | WO 94/06814 | 3/1994 |
| WO | WO 95/19431 | 7/1995 |
| WO | WO 96/12016 | 4/1996 |
| WO | WO 97/06182 | 2/1997 |
| WO | WO 97/06255 | 2/1997 |
| WO | WO 97/26331 | 7/1997 |

OTHER PUBLICATIONS

Birnbaum et al., "An apoptosis–inhibiting gene from a nuclear polyhedrosis virus encoding a polypeptide with Cys/His sequence motifs," J. of Virol., 68:2521–2528 (1994).
Campbell, Monoclonal Antibody Technology, Elsevier Science, Publishers B.V. New York, NY (1984).
Cheng et al., "Staurosporine, K–252a and K–252b stabilize calcium homeostasis and promote survival of CNS neurons in the absence of glucose," J. Neurochem., 62:1319–1329 (1994).
Clem et al., "Anti–apoptotic genes of baculovirus," Cell Death and Differentiation, 3:9–16 (1996).
Clem et al., "Induction and inhibition of apoptosis by insect viruses," Apoptosis II: The Molecular Basis of Apoptosis in Disease, Cold Spring Harbor Laboratory Press, p. 89–110 (1994).
Clem et al., "Prevention of apoptosis by a baculovirus gene during infection of insect cells," Science 254:1388–1390 (1991).
Clem et al., "Control of programmed cell death by the baculovirus genes p35 and IAP," Mol. and Cell. Biology, 14:5212–5222 (1994).
Crook et al., "An apoptosis–inhibiting baculovirus gene with a zinc finger–like motif," J. of Virol., 67:2168–2174 (1993).
Crocker et al., "Adenovirus–mediated NAIP overexpression confers protection against global ischemia," Database Biosis, Abstract (1996).
Dhein et al., "Autocrine T–cells suicide mediated by APO–1 (Fas/CD95)," Abstract, Nature, 373:438–441 (1995).
Duckett et al., "A conserved family of cellular genes related to the baculovirus IAP gene and encoding apoptosis inhibitors," The EMBO Journal, 15:2685–2694 (1996).
Fernandez et al., "Differential sensitivity of normal and Ha–ras–transformed C3H mouse embryo fibroblasts to tumor necrosis factor; Induction of bcl–2, c–myc, and manganese superoxide dismutase in resistant cells," Abstract, Oncogene, 9:2009–2017 (1994).
Ferrari et al., "N–acetylcysteine (D– and L–stereoisomers) prevents apoptotic death of neuronal cells," Abstract, J. Neurosci., 1516:2857–2866 (1995).
Fisher et al., "Dominant interfering Fas gene mutations impair apoptosis in a human autoimmune lymphoproliferative syndrome," Cell, 81:935–946 (1995).
Francis et al., "The response of GABAergic and cholinergic neurons to transient cerebral ischemia," Brain Res., 243:271–278 (1982).
Friedmann, "Overcoming the obstacles to gene therapy," Sci. Am. 276:96–101 (1997).
Gibelli et al., "Tat–expressing Jurkat cells show an increased resistance to different apoptic stimuli including acute human immunodefeciency virus–type–1 (HIV–1) infection," Abstract, Br. J. Haematol., 89:24–33 (1995).
Glicksman et al., "K–252a and staurosporing promote choline acetyltransferase activity in rat spinal cord cultures," J. Neurochem., 61:210–221 (1993).

(List continued on next page.)

Primary Examiner—Anne-Marie Falk
(74) Attorney, Agent, or Firm—Clark & Elbing, LLP; Kristina Bicker-Brady

(57) ABSTRACT

NAIP and IAP polypeptides prevent neuronal cell death caused by ischemia, neurodegenerative conditions, and axotomy. The invention provides methods for neuroprotection by the prevention of cell death and kits and methods for the identification of neuroprotective therapeutic compounds.

19 Claims, 34 Drawing Sheets

OTHER PUBLICATIONS

Glicksman et al., "K–252a analog prevents developmentally programmed motoneuron death and the loss of Chat activity in adult motoneurons in vivo," Soc. Neuro. Abst., 441 (1994).

Glicksman et al., "K–252a promotes survival and choline acetyltransferase activity in striatal and basal forebrain neuronal cultures," J. Neurochem., 64:1502–1512 (1995).

Golstein et al., "Homology between reaper and the cell death domains of Fas and TNFR1," Cell 81:185–186 (1995).

Goruppi et al., "Dissection of c–myc domains involved in S phase induction of NIH3T3 fibroblasts," Abstract, Oncogene, 9:1537–1544 (1994).

Harrington et al., "c–Myc–induced apoptosis in fibroblasts is inhibited by specific cytokines," Abstract, EMBO J. 13:3286–3295 (1994).

Itoh et al., "A novel protein required for apoptosis. Mutational analysis of human Fas antigen," Abstract, J. Biol. Chem., 268:10932–10937 (1993).

Johnstone et al., Immunochemistry in Practice $2^{nd}$ edition, Blackwell Scientific Publications, London (1987).

Katsikis et al., "Fas antigen stimulation induces marked apoptosis of T lymphocytes in human immunodeficiency virus–infected individuals," Abstract, J. Exp. Med., 1815:2029–2036 (1995).

Kerr, "Neglected opportunities in apoptosis research," Trends in Cell Biology, 5:55–57 (1995).

Korsmeyer, "Regulators of cell death," TIG 11:101–105 (1995).

Li et al., "Induction of apoptosis in uninfected lymphocytes by HIV–1 Tat protein," Abstract Science, 268:429–431 (1995).

Liston et al., "Suppression of apoptosis in mammalian cells by NAIP and a related family of IAP genes," Nature, 397:349–353 (1996).

Marsall, "Gene therapy's growing pains," Science 269:1050–1055 (1995).

Martin et al., "HIV–1 infection of human CD4+ T cells in vitro. Differential induction of apoptosis in these cells.," Abstract, J. Immunol., 152:330–342 (1994).

Melino et al., "Tissue transglutaminase and apoptosis: sense and antisense transfection studies with human neuroblastoma cells," Abstract, Mol. Cell. Biol., 14:6584–6596 (1994).

Murayama et al., "Immunocytochemical and ultrastructural studies of Werdnig–Hoffmann disease," Acta Neuropathol., 81:408–417 (1991).

Muro–Cacho et al., "Analysis of apoptosis in lymph nodes of HIV–infected persons. Intensity of apoptosis correlates with the general state of activation of the lymphoid tissue and not with stage of disease or viral burden," Abstract, J. Immunol., 154:5555–5566 (1995).

Nakanshi et al., "K–252a, a novel microbial product, inhibits smooth muscle myosin light chain kinase," J. Biol. Chem., 23:6215–6219 (1988).

Nunez et al., "The Bcl–2 family of proteins: regulators of cell death and survival," Trends in Cell Biology, 4:399–403 (1994).

Orkin et al., Report and recommendations of the panel to assess the NIH investment in research on gene therapy (1995).

Osborne et al., "Essential genes that regulate apoptosis," Trends in Cell Biology, 4:394–399 (1994).

Peterson et al., "Loss of GABAergic neurons in medial septum after fimbria–fornix transection," Neurosci. Lett., 76:140–144 (1987).

Pulsinelli et al., "Temporal profile of neuronal damage in a model of transient forebrain ischemia," Ann. Neurol., 11:491–498 (1982).

Rabizadeh et al., "Expression of the baculovirus p35 gene inhibits mammalian neural cell death," Abstract, J. Neurochem., 61:2318–2321 (1993).

Ridoux et al., "The use of adenovirus vectors for intracerebral grafting of transfected nervous cells," Neuroreport., 5:801–804 (1994).

Ridoux et al., "Adenoviral vectors as functional retrograde neuronal tracers," Brain Res., 648:171–175 (1994).

Ridoux et al., "Ex vivo culture of adult microglial cells from previously lesioned rat brains," C.R. Acad. Sci. III, 317:217–224 (1994).

Rieux–Laucat et al., "Mutations in Fas associated with human lymphoproliferative syndrome and autoimmunity," Science, 268:1347–1349 (1995).

Robertson et al., "Neuroprotective effects of K252a in cerebral ischemia: The NAIP connection," Database Biosis, Abstract (1996).

Rosenbaum et al., "Evidence for hypoxia–induced, programmed cell death of cultured neurons," Abstract, Ann. Neurol., 376:864–870 (1994).

Rothe et al., "The TNFR2–TRAF signaling complex contains two novel proteins related to baculoviral inhibitor of apoptosis proteins," Cell, 83:1243–1252 (1995).

Roy et al., "The gene for neuronal apoptosis inhibitory protein is partially deleted in individuals with spinal muscular atrophy," Cell, 80:167 (1995).

Sato et al., "Neuronal differentiation of PC12 cells as a result of prevention of cell death by bcl–2,"Abstract, J. Neurobiol., 25:1227–1234 (1994).

Sauer et al., "Progressive degeneration of nigrostriatal dopamine neurons following intrastriatal terminal lesions with 6–hydroxydopamine: a combined retrograde tracing and immunocytochemical study in the rat," Neuroscience, 59:401–415 (1994).

Semba et al., "Organization of central cholinergic systems," Progress in Brain Res., 79:36–63 (1989).

Smith–Swintosky et al., "K252A, K252B and staurosporine increase hippocampal neuron survival and improve water maze performance after kainate," Soc. Neuro. Abst., 2130 (1995).

Steiman et al., "Infantile neuronal degeneration masquerading as Werdnig–Hoffmann disease," Ann. Neurol., 8:317–324 (1980).

Steller, "Mechanisms and genes of cellular suicide," Science, 267:1445–1455 (1995).

Talley et al., "Tumor necrosis factor alpha–induced apoptosis in human neuronal cells: Protection by the antioxidant N–acetylcysteine and the genes bcl–2 and crmA," Abstract, Mol. Cell. Biol., 1585:2359–2366 (1995).

Terai et al., "Apoptosis as a mechanism of cell death in cultured T lymphoblasts acutely infected with HIV–1," Abstract, J. Clin. Invest., 87:1710–1715 (1991).

Tetzlaff et al., "Changes in cytoskeletal proteins in the rat facial nucleus following axotomy," J. Neurosci. 8:3181–3189 (1988).

Towfighi et al., "Is Werdnig–Hoffman disease a pure lower motor neuron disorder?," Acta Neuropathol., 65:270–280 (1985).

Verma et al., "Gene therapy—promises, problems, and prospects," Nature 389:239–242 (1997).

Vossbeck et al., "Direct transforming activity of TGF–beta on rat fibroblasts," Abstract, Int. J. Cancer, 61:92–97 (1995).

Walkinshaw et al., "Induction of apoptosis in catecholaminergic PC12 cells by L–DOPA. Implications for the treatment of Parkinson's disease," Abstract, J. Clin. Invest. 95:2458–2464 (1995).

Westendorp et al., "Sensitization of T cells to CD95–mediated apoptosis by HIV–1 Tat and gp120," Nature, 375:497–499 (1995).

White et al., "Genetic control of programmed cell death in drosphila," Science, 264:677–683 (1994).

Williams et al., "Apoptosis: final control point in cell biology," Trends in Cell Biology 2:263–267 (1992).

Wyllie, "Death gets a brake," Nature, 369:272–273 (1994).

Xu et al., "Elevation of neuronal expression of NAIP reduces ischemic damage in the rat hippocampus," Nature Medicine 3:997–1004 (1997).

Xu et al., "Distribution of neuronal apoptosis inhibitory protein–like immunoreactivity in the rat central nervous system," The Journal of Comparative Neurology 382:247–259 (1997).

Effects of Adenovirally-mediated NAIP overexpression on Nigral TH-immunoreactivity following Striatal 6-OHDA
March 1997

Control-Vehicle

LacZ-6-OHDA

NAIP-6-OHDA

AXOTOMIZED

CONTRALATERAL

HIAP-2　　　　　　　XIAP　　　　　　　NAIP 1 day axotomized    contralateral    Hippocamp.

VEH+SHAM

VEH+4VO

K252a+4VO

Fig. 34A  Fig. 34B
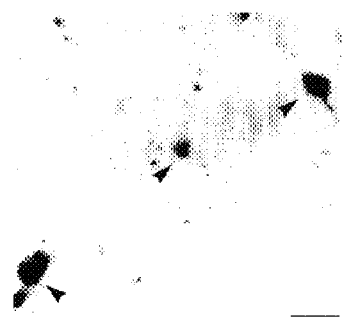
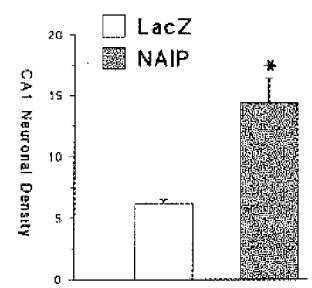
Fig. 34C  Fig. 34D  Fig. 34E

METHODS FOR ENHANCING SURVIVAL OF A NEURON

CROSS REFERENCE TO RELATED APPLICATION

This application is a continuation application of U.S. Ser. No. 08/844,693, filed Apr. 25, 1997, now U.S. Pat. No. 6,159,948 which claims benefit from provisional application No. 60/030,590 filed Nov. 14, 1996 and provisional application No. 60/017,354 filed Apr. 26, 1996.

The field of the invention is neuronal cell death.

BACKGROUND OF THE INVENTION

Neuronal cell death can occur as a result of a variety of conditions including traumatic injury, ischemia, degenerative disease (e.g., Parkinson's disease, ALS, or SMA), or as a normal part of tissue development and maintenance.

We have previously discovered the NAIP and the IAP proteins (see U.S. Ser. No. 08/511,485 now U.S. Pat. No. 5,919,912; Ser. No. 08/576,956 now U.S. Pat. No. 6,156,535; and 60/017,354, incorporated by reference). These proteins are involved in the control of apoptosis.

Developmental cell death, or apoptosis, is a naturally occurring process thought to play a critical role in establishing appropriate neuronal connections in the developing central nervous system (CNS). Apoptosis is characterized morphologically by condensation of the chromatin followed by shrinkage of the cell body. Biochemically, the hallmark of apoptosis is the degradation of nuclear DNA into oligonucleosomal fragments (multiples of 180 basepairs) mediated by a $Ca^{2+}/Mg^{2+}$-dependent endonuclease. DNA laddering precedes cell death and may be a key event leading to death. In keeping with this proposal, agents which inhibit DNA fragmentation prevent apoptosis, whereas morphology indicative of apoptosis is produced by enzymes that digest nuclear DNA. Apoptosis is often dependent on RNA and protein synthesis within the dying cell suggesting the activation of a cell death pathway. The best defined genetic pathway of cell death is in the nematode Caenorhabditis where both effector (ced-3 and ced-4) and repressor (ced-9) genes have been isolated. Similar genes have been identified in mammals. One such example is the proto-oncogene bcl-2 which is thought to be the mammalian homolog of ced-9. Overexpression of Bcl-2 has been shown to render neurons resistant to the damaging effects of a wide variety of noxious treatments. However, the very low levels of Bcl-2 detected in adult brain suggest that other proteins may play a more important role in preventing apoptosis in the mature CNS.

Spinal muscular atrophy (SMA) is a hereditary neurodegenerative disorder characterized by a severe depletion of motor neurons in the spinal cord and brain stem. Many of the motor neurons observed at autopsy in SMA spinal cords display such features as chromatolysis which are consistent with the apoptosis. During maturation of the spinal cord, as many as 50% of motor neurons undergo apoptosis. This has led to the suggestion that a genetic defect in a neuronal apoptotic pathway may be responsible for motor neuron depletion in SMA. Recently two candidate genes, i.e., survival motor neuron (smn) and neuronal apoptosis inhibitory protein (naip), have been identified. The product of the naip gene was termed neuronal apoptotic inhibitory protein (NAIP) because of sequence homology with two baculoviral proteins (Cp-IAP and Op-IAP) that block virally induced apoptosis.

Parkinson's disease (PD) is a progressive neurodegenerative disorder characterized by a loss of nigrostriatal neurons which results in a severe depletion of dopamine (DA) levels in the basal ganglia. Rats which have sustained unilateral lesions of the nigrostriatal pathway produced by the catecholamine-specific neurotoxin, 6-hydroxydopamine (6-OHDA) serve as an animal model of PD. Unilateral injection of 6-OHDA into the medial forebrain bundle or the substantia nigra pars compact results in a rapid degeneration of the nigrostriatal pathway. However, injection of 6-OHDA into the striatum produces a progressive degeneration (>1 week) of the nigrostriatal pathway which is believed to more closely resemble the natural pathology of PD (Sauer and Oertel, 1994). No good treatment for the prevention of PD degeneration currently exists.

Epilepsy is characterized by brain seizures and often results in neural cell death. It has been observed that previously kindled rats, i.e., those rendered "epileptic" via daily application of low intensity electrical stimulation, show considerably less brain damage from kainic-acid induced status epilepticus as compared to naive rats. Status epilepticus (SE) is characterized by continuous electrographic and/or behavioral seizures that occur unabated for greater than 30 minutes. In naive, nonkindled rats, this condition ultimately results in severe neuronal damage in several brain regions. Despite experiencing a form of SE as severe as that observed in a naive rat, the kindled "epileptic" rats show only minimal neuronal loss. Determining the mechanisms responsible for this experience-induced neuroprotection could provide novel approaches to the amelioration of brain damage resulting not only from SE, but also from other neurological traumas such as stroke.

Ischemia results when blood flow to the CNS is interrupted. This is frequently what happens following traumatic injury and stroke. Cell death often results. If this interruption of blood flow effects a large area of the CNS, or lasts for a long period of time, death due to loss of neurological function required for viability occurs. However, if blood flow to the CNS is transiently interrupted and recirculation is established within minutes, only certain neurons in the brain will die.

The best experimental model partial neuronal death due to ischemia is the 4-vessel occlusion model. In this global model of cerebral ischemia, neurons in neocortical layers 3, 5, and 6', small- and medium-sized striatal neurons; and hippocampal CA1 pyramidal neurons are among the most vulnerable (Pulsinelli et al., Ann. Neurol. 11:491–498, 1982). By contrast, cholinergic interneurons in the striatum and CA3 pyramidal neurons in the hippocampus are more resistant to the damaging effects of transient global ischemia (Francis and Pulsinelli, Brain Res. 243:271–278, 1982).

SUMMARY OF THE INVENTION

We have discovered that increased levels of NAIP and IAP polypeptides used provide neuroprotection and allow neural regeneration.

We have found that increased NAIP levels correlate with neuronal survival under a variety of conditions which normally result in neuronal cell death. Furthermore, increased NAIP and IAP levels allow axonal regrowth after axotomy.

Taken together, these findings indicate that NAIP and the IAPs play a key role in conferring resistance to ischemic damage and neural degeneration, and allowing neural repair. Accordingly, our discovery provides both methods for the prevention of neural damage and neural repair and methods by which to screen for neuroprotective and neuroregenerative compounds.

The invention may be summarized as follows.

In the two principle aspects, the invention provides a method for inhibiting death of a cell of the nervous system and/or enhancing neural regeneration. The methods include increasing the biological activity (e.g., levels or neuroprotective effects as described herein) of a polypeptide selected from the group consisting of the NAIP or an TAP. This increasing in cells exposed or likely to be exposed to ischemic conditions is part of the invention if it is sufficient to produce a 20% or greater increase in the likelihood that a cell will survive following an event which normally causes at least a degree of nerve cell death. In some embodiments, the polypeptide is mammalian NAIP, HIAP, HIAP2, or XIAP. Most preferably the polypeptide is NAIP. In one preferred embodiment the polypeptide is a NAIP polypeptide lacking a portion of the carboxy-terminus. In a related embodiment the nerve cell is the CNS, and most preferably, the cell is a neuronal cell known to be susceptible to post-ischemic cell death.

In another embodiment the increasing is by administration of a transgene encoding the NAIP or TAP polypeptide in an expressible genetic construct. The transgene may be in a construct which includes various types of promoters, e.g., a constitutive promoter, a neurofilament promoter, or a regulatable promoter.

The transgene may be in a viral vector, e.g., an adenovirus vector, a herpes virus vector, or a polio virus vector. In preferred embodiments, the transgene encodes a NAIP or an TAP including an amino acid sequence substantially identical to at least one of the amino acid sequences described in the references provided herein; the transgene is administered to the mammal in the region of the ischemic event (preferably intracranially) the transgene is included in a viral vector (for example, a herpesvirus, adenovirus, adeno-associated virus or poliovirus vector); and the ischemia is due to traumatic injury, stroke, myocardial infarction, or mini-stroke.

In another embodiment, the invention includes a method of treating a mammal who has experienced or is at an increased risk for experiencing an ischemic event, neurodegeneration, or axotomy (for example, a stroke Parkinson's disease or surgical injury, respectively), involving administering to the mammal a NAIP or an IAP in an amount sufficient to inhibit cell death and/or allow regeneration, and further features a therapeutic composition having as an active ingredient a NAIP or an IAP, formulated in a physiologically-acceptable carrier.

In yet other embodiments, the increasing may be by directly administering a NAIP or IAP (e.g., HIAP1, HIAP2, or XIAP), or by administering a molecule found to increase NAIP or IAP-biological activity (e.g., K252a-like alkaloid other than K252a, an ATP analog, or a staurosporine-like compound).

The methods may be used to treat patients diagnosed as having had an ischemic event, suspected to have had or diagnosed as having a predisposition to an ischemia event, a degenerative disease, or axon damage. In the therapeutic methods of the invention the therapeutic molecule is most preferably provided as soon as the predisposition to ischemia, degeneration, or damage has first been detected. Nonetheless, the therapy may be provided up to 72 hours after the ischemic effects event. In the case of degeneration or damage, beneficial effects may be obtained a considerable time after the first detection of the condition.

In some embodiments of the assay the cell is a neuronal cell or a related cell such as a glial cell, the cell is in a mammal (e.g., a mouse), or is in culture.

In two other related aspects, the invention features methods of identifying NAIP or an IAP modulatory compounds or compounds which mimic the neuroprotective or neuroregenerative effects. These methods may be used for detection of therapeutics for neuroprotection and nerve regeneration. The first method involves the identification of modulatory compounds that are capable of increasing the expression or stability of a NAIP or an IAP gene mRNAs or polypeptides, involving (a) providing a cell expressing the NAIP or an IAP; and (b) contacting the cell with a candidate compound, an increase in NAIP or an IAP mRNA or protein expression following contact with the candidate compound identifying a modulatory compound. The second method involves the identification of modulatory compounds which are capable of increasing NAIP or an IAP biological activity, involving (a) providing a cell expressing a NAIP or an IAP; and (b) contacting the cell with a candidate compound, a decrease in NAIP or an IAP expression following contact with the candidate compound identifying a modulatory compound. Preferably, the method also includes monitoring the level of neural cell death in the presence of the compound by contacting a cell (preferably a neuronal cell in culture) susceptible to cell death with the compound. A decrease in cell death indicates a compound with increased promise as neuroprotective or neuroregenerative compound. As one skilled in the art can appreciate, increases in NAIP or IAP biological activity can also be done using cell-free systems and solid state assay systems known to one skilled in the art and readily adaptable for this purpose.

In preferred embodiments of both methods, the NAIP or an IAP gene encodes or the NAIP or an IAP and includes an amino acid sequence that is substantially identical to one of the amino acid sequences described in the references provided herein (including NAIP having a carboxy terminal truncation); the candidate compound may be chosen from a compound bank, or more preferably is a K252a-like compound, a staurosporine-like compound, an ATP analog, or a growth factor-like compound (e.g., a neurotrophic compound).

In a related aspect, the invention features a method of treating a mammal who has experienced or is at an increased risk for experiencing an ischemic event, involving administering to the patient a modulatory compound (for example, identified according to the above methods) in an amount effective to reduce the cell deaths in the mammal. Preferably, the modulatory compound acts by increasing NAIP or an IAP gene expression.

Kits for carrying out the above methods are also included in the invention. Such kits preferably include a substantially pure antibody that specifically recognizes and binds a NAIP or an IAP, and may also include means for detecting and quantitating antibody binding. Alternatively, the kit may include all or a fragment of a NAIP or an IAP nucleic acid sequence useful for hybridization purposes, and may also include means for detecting and quantitating NAIP or an IAP RNA hybridization. In yet another alternative the kit may include a cell system or cell-free for monitoring NAIP or IAP expression. Kits may also include instructions sufficient to allow determination of the detection of a neuroprotective or neuroregenerative compound.

By "NAIP or an IAP" is meant an amino acid sequence which has homology to baculovirus inhibitors of apoptosis. For example, NAIP, truncated NAIP, HIAP1, HIAP2 and XIAP are specifically included (see U.S. Ser. No. 08/511, 485, filed Aug. 4, 1995 now U.S. Pat. No. 5,919,912; Ser. No. 08/576,956, filed Dec. 22, 1995 now U.S. Pat. No. 6,156,535; and PCT/IB97/00142, filed Jan. 17, 1997).

Preferably, such a polypeptide has an amino acid sequence which is at least 45%, preferably 60%, and most preferably 85% or even 95% identical to at least one of the amino acid sequences of the NAIP, truncated NAIP, HIAP1, HIAP2, or XIAP described in the references provided herein.

By a "substantially identical" polypeptide sequence is meant an amino acid sequence which differs only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the polypeptide (assayed, e.g., as described herein).

Preferably, such a sequence is at least 85%, more preferably 90%, and most preferably 95% identical at the amino acid level to the sequence described in the references provided herein. For polypeptides, the length of comparison sequences will generally be at least 15 amino acids, preferably at least amino acids, more preferably at least 25 amino acids, and most preferably at least 35 amino acids.

Identity is typically measured using sequence analysis software (e.g., Sequence Analysis Software Package of the Genetics Computer Group, University of Wisconsin Biotechnology Center, 1710 University Avenue, Madison, Wis. 53705). Such software matches similar sequences by assigning degrees of identity to various substitutions, deletions, substitutions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

By "protein" or "polypeptide" is meant any chain of amino acids, regardless of length or post-translational modification (e.g., glycosylation or phosphorylation).

By "substantially pure" is meant a preparation which is at least 60% by weight (dry weight) the compound of interest, e.g., NAIP or an IAP or NAIP or an IAP-specific antibody. Preferably the preparation is at least 75%, more preferably at least 90%, and most preferably at least 99%, by weight the compound of interest. Purity can be measured by any appropriate method, e.g., column chromatography, polyacrylamide gel electrophoresis, or HPLC analysis.

By "increasing biological activity" is meant increasing transcription of the relevant gene, translation of the relevant mRNA, increasing stability of the relevant RNA, modification of the polypeptide to enhance stability, enhancement of neuroprotective or neuroregenerative activity, e.g., in an assay provided herein, and administration of compounds which stabilize the polypeptide.

By "purified DNA" is meant DNA that is not immediately contiguous with both of the coding sequences with which it is immediately contiguous (one on the 5' end and one on the 3' end) in the naturally-occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequence.

By a "substantially identical" nucleic acid is meant a nucleic acid sequence which encodes a polypeptide differing only by conservative amino acid substitutions, for example, substitution of one amino acid for another of the same class (e.g., valine for glycine, arginine for lysine, etc.) or by one or more non-conservative substitutions, deletions, or insertions located at positions of the amino acid sequence which do not destroy the function of the polypeptide (assayed, e.g., as described herein). Preferably, the encoded sequence is at least 45%, more preferably 60%, and most preferably 85% identical at the amino acid level to at least one of the NAIP or IAP sequences provided by the references herein. If nucleic acid sequences are compared a "substantially identical" nucleic acid sequence is one which is at least 85%, more preferably 90%, and most preferably 95% identical to the NAIP or IAP sequences referenced herein. The length of nucleic acid sequence comparison will generally be at least 50 nucleotides, preferably at least 60 nucleotides, more preferably at least 75 nucleotides, and most preferably 110 nucleotides. Again, homology is typically measured using sequence analysis software (e.g., Sequence Analysis Software Package of the Genetics Computer Group, University of Wisconsin Biotechnology Center, 1710 University Avenue, Madison, Wis. 53705).

By "positioned for expression" is meant that the DNA molecule is positioned adjacent to a DNA sequence which directs transcription and translation of the sequence (i.e., facilitates the production of NAIP or an IAP protein).

By "purified antibody" is meant antibody which is at least 60%, by weight, free from the proteins and naturally-occurring organic molecules with which it is naturally associated. Preferably, the preparation is at least 75%, more preferably at least 90%, and most preferably at least 99%, by weight, antibody.

By "specifically binds" is meant an antibody which recognizes and binds a NAIP or an IAP but which does not substantially recognize and bind other molecules in a sample (e.g., a biological sample) which naturally includes NAIP or an IAP. An antibody which "specifically binds" NAIP or an IAP is sufficient to detect a NAIP or an IAP protein product in such a biological sample using one or more of the standard immunological techniques available to those in the art (for example, Western blotting or immunoprecipitation).

By "ischemia" is meant any disruption of blood flow that causes cellular anoxia more rapidly than normal and which leads to cell death. Most ischemia is the result of a partial or complete lack of blood flow. Ischemia according to the invention is preferably ischemia of cells of the CNS, most preferably neuronal cells of the CNS.

By "relative to a wild-type sample" is meant either (a) relative to an equivalent tissue sample from a non-ischemic area of an animal or (b) relative to an non-ischemic cell in culture.

By "immunological methods" is meant any assay involving antibody-based detection techniques including, without limitation, Western blotting, immunoprecipitation, and direct and competitive ELISA and RIA techniques.

By "means for detecting" is meant any one or a series of components that sufficiently indicate a detection event of interest. Such means involve at least one label that may be assayed or observed, including, without limitation, radioactive, fluorescent, and chemiluminescent labels.

By "NAIP or an IAP RNA" is meant messenger RNA transcribed from a NAIP or an IAP DNA sequence.

By "hybridization techniques" is meant any detection assay involving specific interactions (based on complementarity) between nucleic acid strands, including DNA-DNA, RNA-RNA, and DNA-RNA interactions. Such hybridization techniques may, if desired, include a PCR amplification step.

By "transgene" is meant a nucleic acid sequence which is inserted by artifice into a cell and becomes a part of the genome of that cell and its progeny. Such a transgene may be partly or entirely heterologous to the cell.

By "modulatory compound", as used herein, is meant any compound capable of either increasing NAIP or an IAP expression (i.e., at the level of transcription, translation, or post-translation) or increasing NAIP or an IAP protein activity (i.e., by stabilizing the active form of the protein or by otherwise decreasing the amount of apoptosis in a cell type susceptible to apoptosis).

By "ischemic cell death" is meant, loss of cell viability following a decrease or blockage in blood flow to the affected cell.

By "inhibiting cell death" is meant at least a 10% preferably or 20%, increase in the likelihood that a cell will survive following an event which normally causes cell death (relative to an untreated control cell). Preferably, the cells being compared are neural cells normally susceptible to ischemic cell death, neurodegeneration, or axotomy. Preferably, the decrease in the likelihood that a cell will die is 80%, more preferably 2-fold, most preferably, 5-fold.

Abbreviations used herein are as follows: oculomotor nucleus (3); oculomotor nerve root (3nr); facial nucleus (7); vestibulocochlear nerve (8vn); nucleus vagus (10); hypoglossal nucleus (12); cervical 5 (C5); Clarke's column (CC); cuneate nucleus (Cu); dorsal hypothalamal area (DA); dentate gyrus (DG); dorsal medial spinal trigeminal nucleus (DMSP5); endopeduncular nucleus (EP); granule cell layer (G); globus pallidus (GP); gracile nucleus (Gr); Edinger-Westphal nucleus (EW); horizontal diagonal band (HDB); interposed cerebellar nucleus (int);stratum lucunosum (L); lateral cerebellar nucleus (lat); locus coeruleus (LC); lateral hypothalamal area (LH); lateral habenular nuclei (Lhb); stratum moleculare (M); mesencephalic trigeminal nucleus (Me5); medial habenular nuclei (Mhb); motor trigeminal nucleus (Mo5); stratum oriens (O); pyramidal cell layer (P) (FIG. 2); Purkinje cell layer (FIG. 11); pontine nucleus (Pn); principal trigeminal sensory nucleus (Pr5);stratum radiatum (R); red nucleus, magnocellular part (RMC); red nucleus, parvocellular part (RPC); rostral periolivary area (RPO); sacral spinal cord (S); substantia nigra pars compact (SNC); substantia nigra pars reticulata (SNR); substantia nigra pars lateralis (SNL); spinal trigeminal nucleus, oral part (SPO5); ventral cochlear nucleus (VC); vertical diagonal band (VDB); vestibular nucleus (Ve); thoracic 2 (T2); and thoracic 6 (T6).

Other features and advantages of the invention will be apparent from the following detailed description thereof, and from the claims.

BRIEF DESCRIPTION OF THE DRAWING

FIGS. 34A–34E are photographs showing the effects of virally-mediated NAIP overexpression on the loss of CA1 neurons after transient forebrain ischemia. A. Immunohistochemical detection of neurons with a monoclonal antibody (A60) against the neuron-specific marker NeuN in the hippocampus (left side) stereotaxically injected with an adenoviral construct containing lacZ 5 days after 10 min of 4-VO. B. NeuN-like immunoreactivity in the right hippocampus stereotaxically injected with a recombinant adenoviral construct containing myc-tagged NAIP 5 days after 10 min of 4-VO. Note the larger number of CA1 neurons in the hippocampus injected with the NAIP adenovirus. C. CA1 neurons (arrow heads) that display X-gal staining after intrahippocampal injection of the lacZ construct in an animal that was not subjected to 4-VO. D. CA1 neurons (arrow heads) in the NAIP adenovirus-injected side labelled with the mAb9E10 antibody which recognizes myc-tagged NAIP. Scale bars=500 µm (A, B); 50 µm (C, D). E. Quantitative comparisons of the effects of virally-mediated NAIP and lacZ overexpression on the loss of CA1 neurons after transient forebrain ischemia. The density of CA1 neurons expressing NeuN-like immunoreactivity was assessed by computer-assisted image analysis. Neuronal density represents the number of labelled cells per 100 µm length of the CA1 pyramidal layer. Blank regions in the center of the CA1 field represent damage produced by the injection procedure. Cell counts demonstrated that by comparison to the side injected with an adenoviral construct containing lacZ, CA1 loss in the hippocampus injected with the adenovirus construct containing myc-tagged NAIP was reduced by about 60%. Histograms and bars represent mean and the standard error of the mean for 6 animals. Asterisk, significantly different from side injected with lacZ vector ($P<0.01$; t-test).

DESCRIPTION OF THE PREFERRED EMBODIMENTS

Figure 1A:
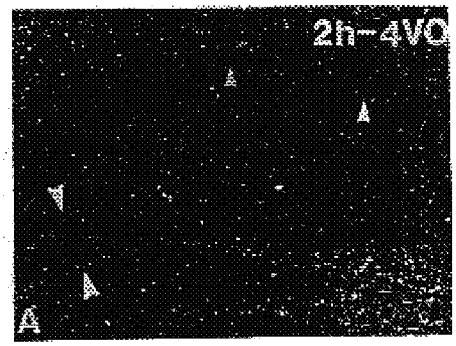
FIGS. 1A–1F are photographs showing detection of NAIP mRNA by in situ hybridization histochemistry in the hippocampus following transient global ischemia (A–E) or sham surgery (F). NAIP mRNA levels are below the limit of detection in hippocampus CA1 neurons (small arrows) and barely detectable in the dentate gyrus (large arrows) at 2 h (A) and 12 h (B) following four-vessel occlusion (4-VO). At 12 h, there is a small increase in NAIP expression in the dentate gyrus (large arrows) (B). At 24 h (C), the hybridization signal is modestly elevated in CA1 neurons (small arrows) and the dentate gyrus (big arrows). NAIP levels remain constant in dentate granule cells (big arrows), but further increased in CA1 neurons (small arrows), 48 h (D) and 72 h (E) following 4-VO. Scale bar=500 μm.
Figure 1D:
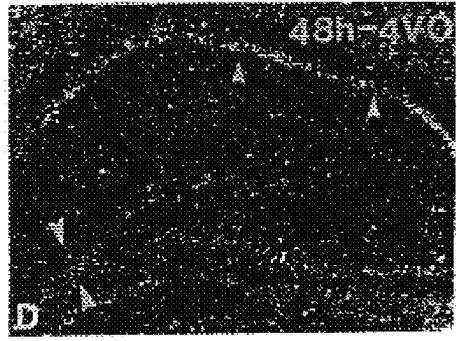
Figure 1B:
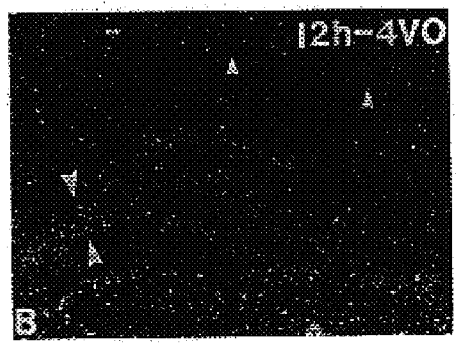
Figure 1E:
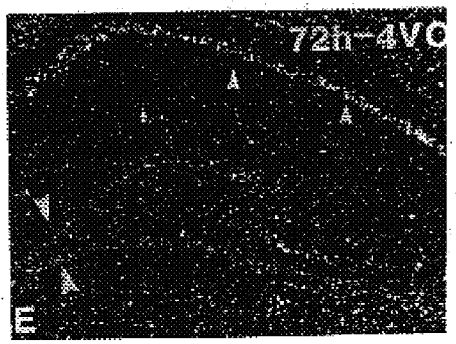
Figure 1C:
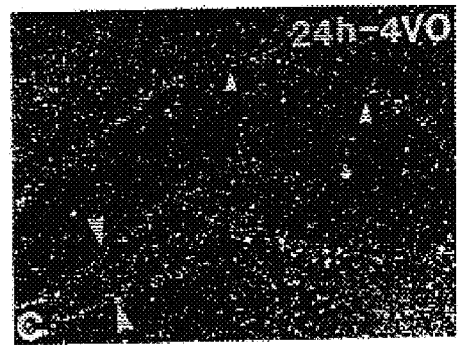
Figure 1F:
Figure 2A:
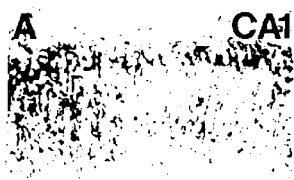
FIGS. 2A–2L are photographs showing NAIP-like immunoreactivity in hippocampal CA1 (A, D, G and J), striatal (B, E, H and K) and thalamic (C, F, I and L) neurons of animals subjected to a sham ischemia procedure (A, B and C) or 10 min of transient forebrain ischemia (D–L). Moderate levels of NAIP-like immunoreactivity were present 24 h after the sham procedure in hippocampal CA1 neurons (CA1; A) and ventolateral thalamus (THAL; C). In striatum (STR; B), high levels of NAIP-like immunoreactivity are exhibited by large cholinergic neurons (large arrow) while very low levels are detected in medium-sized neurons (small arrow). A modest elevation of NAIP-like immunoreactivity occurred in CA1 neurons 3 hr after global ischemia (D) while NAIP levels appeared to be decreased at 24 h (G) and 72 h (J). NAIP-like immunoreactivity appeared elevated in both medium (small arrow) and large (large arrow) sized striatal neurons 3 hr after global ischemia (E). NAIP levels appear to be decreased in medium, but not large (large arrow), neurons at 24 h (H) and 72 h (K). NAIP-like immunoreactivity was dramatically elevated in thalamic neurons 3 h (F) and 24 h (I) after four-vessel occlusion. At 72 h, NAIP-like immunoreactivity still appear to be elevated in thalamic neurons (L). Scale bar=150 μm.
Figure 2B:
Figure 2C:
Figure 2D:
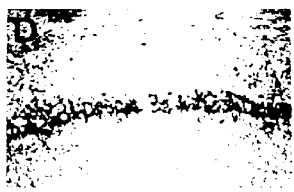
Figure 2E:
Figure 2F:
Figure 2G:
Figure 2H:
Figure 2I:
Figure 2J:
Figure 2K:
Figure 2L:

Mutations in the NAIP protein (neuronal apoptotic inhibitory protein) are associated with spinal muscular atrophy, an autosomal recessive disorder characterized by depletion of spinal cord motor neurons (Roy et al., Cell 80:167–178, 1995). The NAIP gene is homologous to two baculovirus inhibitor of apoptosis proteins (Cp-IAP and Op-IAP) and is partly deleted in individuals with type I spinal muscular atrophy. Overexpression of NAIP protects several different cell lines from apoptotic death induced by a variety of triggers. This finding would seem to indicate that without NAIP there is excessive apoptotic death of motor neurons, the result being spinal muscular atrophy. Consistent with an anti-apoptotic role for NAIP, immunohistochemical analysis indicates NAIP is localized in motor, but not sensory, neurons of the spinal cord.

We have examined the distribution of neurons which express NAIP in the adult forebrain both generally, and under conditions of ischemia and neurodegeneration. Our findings, in concert with the observation that NAIP has anti-apoptotic qualities, have led us to the conclusion the damage resulting from cerebral ischemia and neurodegeneration may be controlled by increasing NAIP levels in neurons that are susceptible to the damaging effects of ischemia. We have also discovered that an increased NAIP level is closely associated with the ability of axons to survive regrow after axotomy. Data obtained with the IAPs indicate that they too have similar neuroprotective and regenerative roles. Thus, the invention provides therapies for neuroprotection and neuronal regrowth under a variety of circumstances. Methods and kits for the detection of compounds which enhance neuroprotection and diagnostic kits for the detection of neurodegenerative diseases is also a part of the invention.

What follows is an overview of our results characterizing and showing the neuroprotective NAIP activity of NAIP, details of the neuroprotective methods, and examples illustrating various aspects of the invention.

NAIP Localization.

We use an affinity purified polyclonal antibody raised against neuronal apoptosis inhibitory protein or NAIP to examine the distribution of NAIP-LI in the CNS. Immunohistochemical detection of NAIP revealed that this anti-apoptotic protein is present within neurons located in a wide variety of structures. NAIP-LI was not detected in non-neuronal cell types such as those associated with the cerebrovasculature or glia suggesting that NAIP is selectively expressed by neurons in the CNS.

In the forebrain, low levels of NAIP-LI were observed in the cortex and hippocampus. Within the cortex, NAIP-LI was observed in both superficial and deep layers. In addition to cell body labelling, NAIP-LI was clearly visible in apical dendrites of pyramidal neurons suggesting that this anti-apoptotic protein is actively transported. NAIP-LI was also widely distributed in the hippocampus where it was detected within pyramidal neurons of CA1-CA3 subfields, interneurons and granule cells of the dentate gyrus. As seen in the cortex, NAIP-LI was localized in both the cell bodies and dendrites of pyramidal neurons. The intensity of NAIP staining appeared to be similar in CA1 and CA3 neurons suggesting that NAIP is not responsible for the well characterized differences in the vulnerability of these neuronal populations to ischemic damage (Francis and Pulsinelli, supra). Within the thalamus, moderate levels of NAIP-LI were observed in a large number of neurons located in ventral and lateral regions of this structure. While NAIP-LI was also present in anterior, intralaminar and medial thalamic nuclei, fewer immunoreactive neurons were detected in these areas. NAIP-LI was enriched within fibers forming a dense network in ventrolateral aspects of the thalamus further suggesting that NAIP is transported from the cell body to dendrites and axons.

In contrast to the cortex, hippocampus and thalamus, NAIP-LI in the striatum and habenula was restricted to a small subpopulation of neurons. In the striatum, double labelling studies revealed that NAIP-LI was expressed exclusively in cholinergic interneurons which account for 1% of the total neuronal population in this structure (Semba and Fibiger, Progress in Brain Res. 79: 37–63, 1989). It is tempting to speculate that the high levels of NAIP-LI observed in these neurons may account in part for their resistance to excitotoxic\ischemic injury (Francis and Pulsinelli, supra). Although NAIP-LI was invariably present within striatal cholinergic neurons, NAIP-LI in the basal forebrain was rarely observed in cholinergic neurons. This finding may have relevance to the observation that within the basal forebrain, non-cholinergic cells are more resistant than cholinergic neurons to retrograde injury produced by axotomy (Peterson et al., Neurosci. Lett. 76: 140–144, 1987).

In addition to the cortex, striatum and thalamus, several other structures implicated in sensory and motor function were found to contain NAIP-positive neurons. These included the globus pallidus, substantia nigra pars compacta, entopeduncular nucleus, pontine nuclei, lateral reticular nucleus, cerebellum and spinal cord. The intensity of NAIP-LI in neurons of these structures suggest that this anti-apoptotic protein may play a role in maintaining their survival. Consistent with this proposal are reports of neuronal degeneration in the thalamus (ventral and lateral nuclei), globus pallidus, substantia nigra, pontine nuclei, cerebellum and spinal cord of severe cases of SMA (Steiman et al., Ann. Neurol. 8: 317–324, 1980. Towfighi et al., Acta Neuropathol. 65: 270–280, 1985. Murayama et al., Acta Neuropathol. 81: 408–417, 1991). The concordance between the distribution of NAIP-LI and neuronal damage in SMA strongly suggests that loss of NAIP contributes to pathology observed in this neurodegenerative disorder.

In cranial nerve nuclei, high levels of NAIP-LI were present in both motor and sensory neurons. ChAT immunohistochemistry was utilized to assist identification of motor neuron populations within the midbrain and brain stem. Double labelling studies revealed that NAIP-LI was frequently located in motor (ChAT positive) neurons of the oculomotor, trochlear, motor trigeminal, facial nucleus, motor nucleus of vagus and hypoglossal nucleus. These studies also demonstrated that NAIP-LI was present within sensory (ChAT negative) neurons of cranial nuclei which contain both motor and sensory neurons such as the facial nucleus (data not shown). Lastly, intense NAIP-LI was found in nuclei associated with sensory function, i.e., Clarke's column, gracile and cuneate nuclei. In further support of a central role for NAIP depletion in SMA, all of these structures display damage in SMA (Steiman et. al. supra; Towfighi et al., supra).

In summary, the NAIP localization study demonstrates that NAIP-LI is widely distributed in the CNS. While low to moderate levels of NAIP-LI were observed in the cortex and hippocampus, intense NAIP-LI was detected within a wide variety of subcortical brain regions. These included the thalamus (ventral and lateral nuclei), basal ganglia (striatum, globus pallidum, endopeduncular nucleus, red nucleus and substantia nigra), cranial nerve nuclei, brain stem relay nuclei (cuneate, gracile, pontine, lateral reticular, interpeduncular, olivary nucleus and locus coeruleus), cerebellum and spinal cord. Except for the striatum, all of these regions display neuropathology in severe cases of SMA. The fact that NAIP-LI in the striatum is located exclusively in cholinergic interneurons which account for only 1% of the striatal neuron population may account for the failure of previous studies to observe degenerative changes in this structure (Towfighi et al., supra; Murayama et al., supra).

Transient Ischemia Increases NAIP Levels.

Measurement of NAIP message by in situ hybridization histochemistry indicates that very low levels of mRNA are present in the hippocampus. Indeed, basal expression of NAIP mRNA is only detectable in dentate granule cells of the hippocampus. However, transient cerebral ischemia produced a delayed, but profound, elevation of NAIP expression principally in CA1 neurons. These increases were first apparent 24 h after 10 min of transient forebrain ischemia with peak elevations occurring at 72 h. Despite these large elevations of NAIP mRNA, NAIP-I does not appear to increase in CA1 neurons. In contrast, NAIP-I is reduced below basal levels in CA1 neurons 72 h after recirculation. These findings are consistent with earlier reports demonstrating that protein synthesis is severely depressed in CA1 neurons after transient global ischemia (Thilman et al., Acta. Neuropathol. 71:88–93, 1986; Maruno and Yanagihara, Neurosci. Lett. 115:155–160, 1990; Widmann et al., J. Neurochem. 56:789–796, 1991). Moreover, they suggest that a failure of CA1 neurons to manufacture NAIP protein after transient ischemic attack may render the neurons susceptible to the injurious effects of this noxious treatment.

Unlike the hippocampus, NAIP-I immunoreactivity was dramatically increased in striatal cholinergic neurons 3 h after the ischemic insult. We believe that the resistance of these neurons to the damaging effects of transient cerebral ischemia may be conferred by an ability to increase NAIP expression after an ischemic insult. Similarly, the large increase in NAIP-I detected in thalamic neurons after a short period of global ischemia also appears to contribute to the greater resistance of these neurons to ischemic damage as compared to medium-sized striatal and CA1 neurons (Pulsinelli et al., 1982, supra).

Increasing NAIP Levels Prior to Ischemia Injury Enhances Neuronal Survival.

A major finding of the present invention is that pretreatment with the neuroprotective compound K252a increases levels and reduces CA1 loss after 10 min of transient cerebral ischemia. Our results indicate that ischemic damage in the hippocampus was decreased by administration of K252a once daily (0.1 mg/kg, s.c.) for seven days prior to four-vessel occlusion (4-VO) and each day afterwards. One interpretation of this finding is that K252a pretreatment elevates expression of protective protein(s) which render CA1 neurons more resistant to the injurious effects of transient cerebral ischemia. Consistent with this proposal, we observe elevated levels of both NAIP mRNA and NAIP protein in the hippocampus after acute administration of K252a (0.1 mg/kg, s.c.). We therefore believe that the ability of K252a to increase NAIP levels contributes to its neuroprotective actions.

We also find that K252a increases NAIP levels in the striatum, thalamus and spinal cord. This indicates that this compound also exerts a neuroprotective effect in these regions via enhanced NAIP expression.

We believe that K252a acts by increasing NAIP levels. Accordingly, methods which increase IAP and NAIP protein levels directly or via gene therapy may be used to prevent neuronal death following ischemia. In addition, IAP and NAIP gene expression and biological activity may be monitored as a method for identifying compounds which prevent central nervous system cell death resulting from ischemia.

Correlation of NAIP Expression and Resistance to Ischemic Injury.

Transient cerebral ischemia dramatically elevated NAIP-like (NAIP-LI) immunoreactivity in striatal cholinergic neurons, whereas NAIP-LI in medium spiny neurons in the striatum did not appear to be appreciably increased by this insult. With the notable exception of neurons in the reticular nucleus of the thalamus, neuronal labelling in ventral and lateral aspects of the thalamus was also substantially increased by a short period of global ischemia. Consistent with reports of depressed protein synthesis in CA1 neurons after transient global ischemia (Thilman et al., *Acta Neuropathol.* 71:88–93, 1986; Maruno et al., *Neurosci. Lett.* 115:155–160, 1990; and Widman et al., *J. Neurochem.* 56:789–796, 1991), 4-VO did not elevate NAIP-LI in these neurons but rather a reduction in immunoreactivity was observed 72 h after recirculation. Hence, those neuronal populations known to be susceptible to the damaging effects of transient global ischemia such as striatal medium spiny, thalamic reticular and hippocampal CA1 neurons (Pulsinelli et al., *Ann. Neurol.* 11:491–498, 1982; and Smith et al., *Acta Neuropathol.* (*Berl*) 64:319–332, 1984) failed to display elevated NAIP-LI after 10 minutes of 4-VO. In contrast, we observed large increases in levels of this anti-apoptotic protein in striatal cholinergic and thalamic neurons which are resistant to the injurious effects of a transient ischemic attack (Pulsinelli et al., *Ann. Neurol.* 11:491–498, 1982; and Smith et al., *Acta Neuropathol.* (*Berl*) 64:319–332, 1984). We therefore believe that the susceptibility of these neuronal populations to the damaging effects of transient cerebral ischemia may be determined, at least in part, by their ability to increase NAIP levels after an ischemic insult.

K252a Reduces Ischemic Damage and Elevates NAIP Expression.

A major finding of the present study was the ability of pretreatment with the neuroprotective compound K252a to reduce CA1 loss after 10 min of transient cerebral ischemia. Our results indicate that ischemic damage in the hippocampus was decreased by administration of K252a once daily (0.1 mg/kg, s.c.) for seven days prior to 4-VO and each day afterwards. Since CA1 neuron loss was examined 5 days after 4-VO, further studies will be required to confirm that the neuroprotective effects of K252a are not transient. Administration of K252a did not alter blood pressure, gases ($pCO_2$ and $pO_2$) or pH indicating that it did not reduce CA1 loss by altering these physiological variables. The fact that chronic treatment with K252a was required to decrease ischemic damage suggests that pretreatment may elevate the expression of protective protein(s) which render CA1 neurons more resistant to the injurious effects of transient cerebral ischemia. Consistent with this proposal, we observed that acute administration of K252a (0.1 mg/kg, s.c.) elevated both NAIP mRNA and protein levels in the hippocampus. Moreover, chronic administration of K252a (0.1 mg/kg, s.c., once daily for 7 days) produced a larger elevation of NAIP mRNA and protein levels than seen after a single administration of this compound (0.1 mg/kg, s.c.). It is therefore possible that the larger increases in NAIP levels we have observed after chronic compared to acute treatment with K252a may have relevance for reports indicating that repeated K252a administration produces greater neuroprotection than a single administration of this compound (Smith-Swintosky et al., *Exp. Neurol.* 141:287–296, 1996). Acute administration of K252a also increased NAIP levels in the striatum, thalamus and spinal cord suggesting that this compound may also exert neuroprotective actions in these regions through enhanced NAIP expression. In keeping with this hypothesis, K252a has been shown to have neurotrophic-like effects on primary cultures of striatal and spinal motor neurons (Glicksman et al., *J. Neurochem.* 61:210–221, 1993; and Glicksman et al., *J. Neurochem.* 64:1502–1512, 1995).

The pathways by which K252a upregulates NAIP expression remain to be determined. Several lines of evidence suggests that K252-like compounds exert their beneficial effects by activating growth factor receptor-linked tyrosine kinases. First, K252a can imitate some of the biological effects of NGF (Nakanishi et al., *J. Biol. Chem.* 23:6215–6219, 1988) and can stimulate tyrosine phosphorylation (Maroney et al., *J. Neurochem.* 64:540–549, 1995). Second, using an antiphosphotyrosine antibody, exposure of hippocampal cultures to low concentrations of K252a (100 pM) and K252b, a 9-carboxylic acid derivative of K252a, (100 pM) have been shown by Western blotting to enhance tyrosine phosphorylation of multiple proteins ranging in molecular weight from 40 to 200 kDa (Cheng et al., *J. Neurochem.* 62:1319–1329, 1994). Third, the neuroprotective effects of K252-like compounds were blocked by the selective tyrosine kinase inhibitor genistein but not by its inactive analog genistin (Cheng et al., *J. Neurochem.* 62:1319–1329, 1994).

Virally-mediated NAIP Overexpression is Neuroprotective.

An adenoviral construct capable of overexpressing NAIP in vivo was used to determine whether increasing levels of this anti-apoptotic protein reduced the damaging effects of transient forebrain ischemia in the hippocampus. As a control, an adenoviral construct containing the bacterial enzyme lacZ was injected into the hippocampus in the opposite side of the brain. Cell counts revealed that the NAIP adenovirus increased CA1 neuron survival after an episode of transient forebrain iscehmia. Since NAIP generated from the adenoviral construct was Myc tagged, it was possible to identify infected cells by immunohistochemistry using an antibody that selectively recognizes the Myc antigen. Immunohistochemical detection of Myc demonstrated that CA1 neurons were infected by the NAIP adenovirus. However, cell counts revealed that fewer CA1 neurons were infected with the NAIP adenovirus (7±1) than were actually protected from the ischemic insult (15±2). This discrepancy may be explained in at least three ways. Firstly, it is possible that overexpression of NAIP in only a few CA1 neurons is sufficient to prevent a chain event resulting in the widespread loss of CA1 neurons after transient global ischemia. Secondly, it is possible that low levels of NAIP generated by weak infection with the adenovirus are neuroprotective. Such low levels of adenovirally derived NAIP (Myc-tagged) may have been below the detection limit of the Myc antibody as assessed by immunohistochemistry. Thirdly, we have observed that adenoviral infection was not restricted to CA1 neurons. Several other cell types in the hippocampus such as glia and interneurons also appeared to have been infected with the NAIP adenovirus (data not shown). Consequently, NAIP overexpression in these cellular populations may have had a beneficial action which indirectly enhanced the resistance of CA1 neurons to ischemic damage.

Neuroprotective Compounds Function by Increasing NAIP Levels.

Several growth factors including neurotrophins, insulin-like growth factors, and fibroblast growth factors have been shown to protect cultured neurons against excitotoxic/ischemic injury (Mattson et al., *Exp. Neurol.* 124:89–95, 1993). However, clinical application of growth factors for the treatment of stroke is limited by their poor penetration of the blood-brain barrier. A potential solution to this problem is the use of low-molecular-weight compounds which readily cross the blood-brain barrier and mimic the neuroprotective effects of growth factors. One such compound is the bacterial alkaloid K252a which has been shown to exert neuroprotective effects in vitro at low concentrations (fM-nM) (Kase et al., J. Antiobiot 39:1059–1065, 1986; Knusel and Hefti, J. Neurochem. 59(6):1987–1996, 1992). In primary hippocampal, cortical and septal cultures, K252a protects against glucose deprivation-induced neuronal injury (Cheng et al., J. Neurochem. 62:1319–1329, 1994). K252a has also been reported to have neurotrophic-like activity as measured by enhancement of choline acetyltransferase (ChAT) activity in embryonic rat spinal cord cultures (Glicksman et al., J. Neurochem. 61:210–221, 1993; Glicksman et al., J. Neurochem. 64(4):1502–1512, 1995). In keeping with these in vitro findings, an analog of K252a (CEP1347), prevents developmentally programmed motoneuron death and loss of ChAT in adult motoneurons in vivo (Glicksman et al., Soc. Neuro. Abst. 441, 1994). With respect to the hippocampus, a single systemic administration of K252a attenuates the loss of CA3 neurons produced by intrahippocampal injection of kainic acid (Smith-Swintosky et al., Soc. Neuro. Abst. 2130, 1995). Considerably greater protection than that observed after a single pretreatment is produced by chronic administration of K252a for 2 months (Smith-Swintosky et al., 1995, supra). Since excitotoxic mechanisms have been implicated in ischemic cell death, we determined whether pretreatment with K252a reduces the loss of CA1 hippocampal neurons after transient global ischemia. We theorized that K252a may be neuroprotective by inducing NAIP expression. Accordingly, we examined the effects of K252a administration on NAIP expression in the thalamus, hippocampus, striatum and spinal cord.

Immunohistochemical detection of NAIP reveals that, in addition to the spinal cord, this anti-apoptotic protein is present in variety of forebrain structures such as the cortex (i.e., pyramidal neurons), hippocampus, thalamus, and striatum. Hippocampal NAIP-I was located in CA1, CA2, CA3 and CA4 pyramidal neurons and as well as granule cells of the dentate gyrus. Within the thalamus, NAIP-I appeared to be displayed primarily by neurons in the ventral-medial and ventral-lateral aspects of this structure. Given that NAIP is a potent inhibitor of apoptotic death, we believe that NAIP depletion accounts for thalamic abnormalities observed in spinal muscular atrophy (Murayama et al., Acta. Neuropathol. 81:408–417, 1991). NAIP-I in the striatum is restricted to about 1% of the neuronal population. Immunohistofluorescence double labelling demonstrates that striatal NAIP-I is localized exclusively in cholinergic neurons. These cells are known to be interneurons and to account for approximately 1% of the total striatal neuronal population (Semba and Fibiger, Progress in Brain Res. 79:37–63, 1989).

Summary

Our findings suggest that small molecular weight compounds, such as K252a, can penetrate the blood-brain barrier after peripheral administration in sufficient amounts to produce neuroprotective actions. Moreover, results of the present study indicate that these compounds exert their beneficial actions by elevating levels of the anti-apoptotic protein NAIP. Thus, immunohistochemical detection of NAIP may serve as an inexpensive and rapid in vivo method for identification of putative neuroprotective compounds. Furthermore, elevating NAIP levels is an important therapeutic approach to obtaining neuroprotection. This insight into the molecular basis of neuronal survival, reveals novel strategies for the development of better treatments for neurodegenerative disease.

NAIP and IAP Levels are Enhanced in Cells That Survive Axotomy.

In addition to the above, we have found that NAIP and XIAP levels are increased in those cells that survive axotomy. This indicates these proteins (and compounds which enhance their biological activity) may be used to facilitate nerve repair.

Therapies for Preventing or Mitigating Cell Death Following Central Nervous System Ischemic Events.

On the basis of our findings, we conclude that absence of sufficient NAIP or IAP polypeptides is a primary pathogenic mechanism for neuronal death following ischemic insult or during the progression of neurodegenerative disease. Therapeutic measures that increase the levels of NAIP or levels of an IAP will prevent or mitigate the devastating cell death that often occurs as a part of these conditions. These therapeutic approaches are also appropriate for the treatment of presymptomatic individuals with an increased likelihood for experiencing ischemia or a neurodegenerative disease. For example, it may be useful to provide increased protein activity to patients who have experienced an ischemic event, e.g., patients who have experienced traumatic injury, stroke, myocardial infarction, transient ischemic attacks, or any other condition which limits blood flow to the tissues of the CNS. Those at increased risk due to hereditary conditions are also candidates for such treatment. A therapy which increases the levels of NAIP or IAP biological activity may also be provided to patients who are at risk for a condition which may compromise blood flow to the CNS. For example, patients with a history of stroke and patients undergoing intercranial surgery may benefit from prophylactic NAIP or IAP therapy.

i) NAIP or an IAP Gene Therapy

Because expression of NAIP correlates with increased cell survival following ischemia, NAIP and the related IAP genes also find use in neuroprotective gene therapy.

Retroviral vectors, adenoviral vectors, adeno-associated viral vectors, poliovirus vectors, or other viral vectors with the appropriate tropism for cells subject to ischemia cell death or neurodegeneration (for example, viruses with a trophism for striatal neurons or neocortical layers 3, 5, and 6' neurons) may be used as a gene transfer delivery system for a therapeutic NAIP or an IAP gene construct. Numerous vectors useful for this purpose are generally known (Miller, Human Gene Therapy 15–14, 1990; Friedman, Science 244:1275–1281, 1989; Eglitis and Anderson, BioTechniques 6:608–614, 1988; Tolstoshev and Anderson, Current Opinion in Biotechnology 1:55–61, 1990; Sharp, The Lancet 337:1277-1278, 1991; Cornetta et al., Nucleic Acid Research and Molecular Biology 36:311–322, 1987; Anderson, Science 226:401–409, 1984; Moen, Blood Cells 17:407–416, 1991; and Miller and Rosman, Biotechniques 7:980–990, 1989; Le Gal La Salle et al., Science 259:988–990, 1993; and Johnson, Chest 107:77S-83S, 1995). Viral vectors are particularly well developed and have been used in clinical settings.

Non-viral approaches may also be employed for the introduction of therapeutic DNA into cells otherwise likely to die following an ischemic or neurodegenerative event. For example, NAIP or an IAP may be introduced into a neuronal cell by the techniques of intracranial lipofection (Felgner et al., Proc. Natl. Acad. Sci. USA 84:7413, 1987; Ono et al., Neuroscience Lett 117:259, 1990; Brigham et al., Am. J. Med. Sci. 298:278, 1989; Staubinger and Papahadjopoulos, Meth. Enz. 101:512, 1983);

asialorosonucoid-polylysine conjugation (Wu and Wu, J. Biol. Chem. 263:14621, 1988; Wu et al., J. Biol. Chem. 264:16985, 1989); or, less preferably, microinjection under surgical conditions (Wolff et al., Science 247:1465, 1990).

For any of the above approaches, the therapeutic NAIP or an IAP DNA construct is preferably applied to the site of the ischemic or neurodegenerative event (for example, by intracranial injection), but may also be applied to tissue in the vicinity of the event or even to a blood vessel supplying the area near the event.

In the gene therapy constructs, NAIP or an IAP cDNA expression is directed from any suitable promoter (e.g., the human cytomegalovirus, simian virus 40, or metallothionein promoters), and its production is regulated by any desired mammalian regulatory element. For example, if desired, enhancers known to direct preferential gene expression in neuronal cells or anoxic cells may be used to direct expression of NAIP or an IAP expression.

Alternatively, if a NAIP or an IAP genomic clone is utilized as a therapeutic construct NAIP or an IAP expression is preferably regulated by regulatory sequences derived from a heterologous source, e.g., any of the promoters or regulatory elements described above.

Less preferably, NAIP or an TAP gene therapy is accomplished by direct administration of the NAIP or an TAP mRNA to the region of the ischemic event. This mRNA may be produced and isolated by any standard technique, but is most readily produced by in vitro transcription using a NAIP or an TAP cDNA under the control of a high efficiency promoter (e.g., the T7 promoter). Administration of NAIP or an IAP mRNA to cells is carried out by any of the methods for direct nucleic acid administration described above and generally known.

Ideally, the production of NAIP or an IAP protein by any gene therapeutic approach described above results in a cellular level of NAIP or an IAP that is at least equivalent to the cellular level of NAIP or an IAP in cells which normally survive ischemia or other events known to cause neuronal cell death. Treatment by any NAIP or an IAP-mediated gene therapy approach may be combined with more traditional anti-ischemic or neuroprotective therapies.

Fragments or derivatives of the NAIP, HIAP1, HIAP2, or XIAP polypeptides may also be administered by retroviral gene transfer therapy or another suitable viral vector system. Useful fragments or derivatives of NAIP, HIAP1, HIAP2, or XIAP may be adminstered by inserting the nucleic acids encoding these fragments or derivatives in place of the complete NAIP, HIAP1, HIAP2, or XIAP gene in a gene therapy vector, as described above. Such constructs may be tested using the methods for testing the effects of NIAP on ischemia as provided elsewhere herein.

ii) Administration of NAIP or IAP Polypeptides.

Wild-type NAIP or IAP polypeptides may be administered to patients who have or are likely to experience an ischemic event. Useful polypeptides for this method are those which, when provided to the patient, causes a two-fold or more increase in NAIP or IAP biological activity and which thereby provides a neuroprotective effect.

NAIP or IAP polypeptides or nucleic acids altered in the laboratory for therapeutic use may also be administered.

Proteins in which the NAIP or IAP polypeptide is fused to a ligand may be used for the purpose of stabilizing and/or targeting the useful neuroprotective polypeptides. A fusion protein consisting of NAIP or an IAP polypeptide, fused to, for example, tetanus toxin, calcium channel blocking agents, transferrin, poliovirus epitopes, neuropeptide fragments, or steroid hormone androgens, or a fragments thereof which are sufficient to target the protective polypeptide to the neurons of the patient may be used.

iii) Administration of Compounds Which Increase NAIP or IAP Activity in the CNS.

Compounds which are staurosporine-like, K252a-like alkoids (excluding K252a), ATP analogs, or protein kinase inhibitors may be screened for the ability to increase NAIP or IAP polypeptides and, if effective, be administered to patients at risk for, or who have suffered from, ischemia or, neurodegeneration, or traumatic injury. Methods for identifying such compounds are provided below.

A NAIP or an IAP modulator may be administered with a pharmaceutically-acceptable diluent, carrier, or excipient, in unit dosage form. Conventional pharmaceutical practice may be employed to provide suitable formulations or compositions to administer NAIP or an IAP to patients suffering from, at risk for, or presymptomatic for ischemia, neurodegeneration, or traumatic injury. Any appropriate route of administration may be employed, for example, intracranial, parenteral, intravenous, subcutaneous, intramuscular, intraorbital, ophthalmic, intraventricular, intracapsular, intraspinal, intracisternal, intraperitoneal, intranasal, aerosol, or oral administration. Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful intracranial delivery systems for NAIP or an IAP modulatory compounds include pumps, implantable infusion systems, and liposomes.

If desired, treatment with a NAIP or an IAP modulatory compound may be combined with more traditional anti ischemic therapies.

iv) Preventive NAIP or an IAP Therapy

In a patient diagnosed to be susceptible to the occurrence of an event requiring neuroprotection, any of the above therapies may be administered before the occurrence of the event. In particular, compounds shown to increase NAIP or IAP expression or NAIP or IAP biological activity may be administered by any standard dosage and route of administration (see above). Alternatively, gene therapy using a NAIP or IAP expression construct may be undertaken to prevent neural death or damage.

Screens for Neuroprotective Compounds Which Increase NAIP or IAP Activity.

By monitoring NIAP or IAP gene expression or NIAP or IAP protein upon exposure to a test compound one may determine if such a compound is a potential anti-ischemic therapeutic. According to one approach, candidate molecules are added at varying concentrations to the culture medium of cells expressing NAIP or an IAP mRNA. NAIP or an IAP expression is then measured, for example, by standard Northern blot analysis (Ausubel et al., supra) using a NAIP or an IAP cDNA (or cDNA fragment) as a hybridization probe. The level of NAIP or an IAP expression in the presence of the candidate molecule is compared to the level measured for the same cells in the same culture medium but in the absence of the candidate molecule.

If desired, the effect of candidate modulators on expression may, in the alternative, be measured at the level of NAIP or an IAP protein production using the same general approach and standard immunological detection techniques, such as Western blotting or immunoprecipitation with a NAIP or an IAP-specific antibody.

Candidate modulators may be purified (or substantially purified) molecules or may be one component of a mixture of compounds (e.g., an extract or supernatant obtained from cells; Ausubel et al., supra). In a mixed compound assay, NAIP or an IAP expression is tested against progressively smaller subsets of the candidate compound pool (e.g., produced by standard purification techniques, e.g., HPLC or FPLC) until a single compound or minimal compound mixture is demonstrated to modulate NAIP or an IAP expression.

Candidate NAIP or an IAP modulators include peptide as well as non-peptide molecules (e.g., peptide or non-peptide molecules found, e.g., in a cell extract, mammalian serum, or growth medium on which mammalian cells have been cultured). Particularly useful modulators of NAIP or an IAP expression include staurosporine-like compounds, K252a-like compounds, ATP analogs, and protein kinase inhibitors.

A molecule which promotes an increase in NAIP or an IAP expression or NAIP or an IAP protective activity is considered particularly useful in the invention; such a molecule may be used, for example, as a therapeutic.

Modulators found to be effective at the level of NAIP or an IAP expression or activity may be confirmed as useful in animal models and, if successful, may be used as anti-ischemic therapeutics. Preferably, such compounds are neuroprotective.

Sequence of NAIP and the IAP Proteins and Nucleic Acids.

Figure 11:
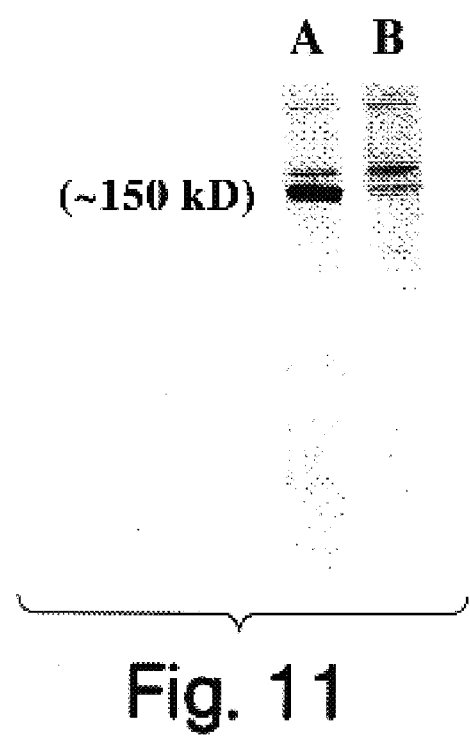
FIG. 11 is a western blot showing analysis of antisera for neuronal apoptosis inhibitory protein (NAIP). Nitrocellulose stripes electrophoretically transferred with whole cell extracts from rat brains were blotted with either NAIP antisera or NAIP antisera which had been preabsorbed with glutathione-S-transferase (GST)-NAIP fusion protein. The affinity-purified NAIP antibody recognized a single band at 150 kD corresponding to the predicted molecular weight for NAIP (lane A). Preabsorption of the antibody with GST-NAIP fusion protein eliminated the 150 kD band (lane B). Each lane was loaded with 20 μg of protein.

The sequence of the NAIP gene is described in FIG. 11 and United Kingdom Application Ser. No. 9421010.2 filed Oct. 18, 1994 and PCT/IB97/00142 filed Jan. 17, 1997. The IAPs are described in U.S. Ser. No. 08/511, 485, filed Aug. 4, 1995 now U.S. Pat. No. 5,919,912 and U.S. Ser. No. 08/576,956, filed Dec. 22, 1995 now U.S. Pat. No. 6,156, 535.

NAIP and IAP Protein Expression.

In general, NAIP and IAP proteins according to the invention may be produced by transformation of a suitable host cell with all or part of a NAIP or an IAP or an IAP-encoding cDNA fragment (e.g., the cDNA described above) in a suitable expression vehicle.

Those skilled in the field of molecular biology will understand that any of a wide variety of expression systems may be used to provide the recombinant protein. The precise host cell used is not critical to the invention. The NAIP or an IAP protein may be produced in a prokaryotic host (e.g., *E. coli*) or in a eukaryotic host (e.g., *Saccharomyces cerevisiae*, insect cells, e.g., Sf21 cells, or mammalian cells, e.g., COS 1, NIH 3T3, or HeLa cells). Such cells are available from a wide range of sources (e.g., the American Type Culture Collection, Rockland, Md.; also, see, e.g., Ausubel et al., *Current Protocols in Molecular Biology*, John Wiley & Sons, New York, 1994). The method of transformation or transfection and the choice of expression vehicle will depend on the host system selected. Transformation and transfection methods are described, e.g., in Ausubel et al. (supra); expression vehicles may be chosen from those provided, e.g., in *Cloning Vectors: A Laboratory Manual* (P. H. Pouwels et al., 1985, Supp. 1987).

One preferred expression system is the baculovirus system (using, for example, the vector pBacPAK9) available from Clontech (Palo Alto, Calif.). If desired, this system may be used in conjunction with other protein expression techniques, for example, the myc tag approach described by Evan et al. (Mol. Cell Biol. 5:3610–3616, 1985).

Alternatively, a NAIP or IAP is produced by a stably-transfected mammalian cell line. A number of vectors suitable for stable transfection of mammalian cells are available to the public, e.g., see Pouwels et al. (supra); methods for constructing such cell lines are also publicly available, e.g., in Ausubel et al. (supra). In one example, cDNA encoding the NAIP or IAP protein is cloned into an expression vector which includes the dihydrofolate reductase (DHFR) gene. Integration of the plasmid and, therefore, the NAIP or an IAP protein-encoding gene into the host cell chromosome is selected for by inclusion of 0.01–300 μM methotrexate in the cell culture medium (as described in Ausubel et al., supra). This dominant selection can be accomplished in most cell types. Recombinant protein expression can be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHFR and pAdD26SV(A) (described in Ausubel et al., supra). Any of the host cells described above or, preferably, a DHFR-deficient CHO cell line (e.g., CHO DHFR− cells, ATCC Accession No. CRL 9096) are among the host cells preferred for DHFR selection of a stably-transfected cell line or DHFR-mediated gene amplification.

Once the recombinant NAIP or IAP protein is expressed, it is isolated, e.g., using affinity chromatography. In one example, an anti-NAIP or an IAP protein antibody (e.g., produced as described herein) may be attached to a column and used to isolate the NAIP or an IAP protein. Lysis and fractionation of NAIP or an IAP protein-harboring cells prior to affinity chromatography may be performed by standard methods (see, e.g., Ausubel et al., supra).

Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980).

Polypeptides of the invention, particularly short NAIP or an IAP protein fragments, can also be produced by chemical synthesis (e.g., by the methods described in *Solid Phase Peptide Synthesis*, 2nd ed., 1984 The Pierce Chemical Co., Rockford, Ill.).

These general techniques of polypeptide expression and purification can also be used to produce and isolate useful NAIP or an IAP fragments or analogs (described herein).

Other Embodiments

In other embodiments, the invention includes any protein which is substantially identical to a drosophila, mouse, or human NAIP or an IAP polypeptides; such homologs include other substantially pure naturally-occurring NAIP or an IAP proteins as well as allelic variants; natural mutants; induced mutants; proteins encoded by DNA that hybridizes to the NAIP or an IAP DNA sequences described herein under high stringency conditions or, less preferably, under low stringency conditions (e.g., washing at 2×SSC at 40° C. with a probe length of at least 40 nucleotides); and proteins specifically bound by antisera directed to a NAIP or an IAP polypeptide. The term also includes chimeric polypeptides that include a NAIP or an IAP portion.

The invention further includes the use of analogs of any naturally-occurring NAIP or an IAP polypeptide. Analogs can differ from the naturally-occurring NAIP or an IAP protein by amino acid sequence differences, by post-translational modifications, or by both. Analogs of the invention will generally exhibit at least 85%, more preferably 90%, and most preferably 95% or even 99% identity with all or part of a naturally-occurring NAIP or an IAP amino acid sequence. The length of sequence comparison is at least 15 amino acid residues, preferably at least 25 amino acid residues, and more preferably more than 35 amino acid residues. Modifications include in vivo and in vitro chemical derivatization of polypeptides, e.g., acetylation, carboxylation, phosphorylation, or glycosylation; such modifications may occur during polypeptide synthesis or processing or following treatment with isolated modifying enzymes. Analogs can also differ from the naturally-occurring NAIP or an IAP polypeptide by alterations in primary sequence. These include genetic variants, both natural and induced (for example, resulting from random mutagenesis by irradiation or exposure to ethanemethylsulfate or by site-specific mutagenesis as described in Sambrook, Fritsch and Maniatis, *Molecular Cloning: A Laboratory Manual* (2d ed.), CSH Press, 1989, or Ausubel et al., supra). Also included are cyclized peptides, molecules, and analogs which contain residues other than L-amino acids, e.g., D-amino acids or non-naturally occurring or synthetic amino acids, e.g., β or γ amino acids.

In addition to full-length polypeptides, the invention also includes use of NAIP or an IAP polypeptide fragments. As used herein, the term "fragment," means at least 20 contiguous amino acids, preferably at least 30 contiguous amino acids, more preferably at least 50 contiguous amino acids, and most preferably at least 60 to 80 or more contiguous amino acids. Fragments of NAIP or an IAP polypeptides can be generated by methods known to those skilled in the art or may result from normal protein processing (e.g., removal of amino acids from the nascent polypeptide that are not required for biological activity or removal of amino acids by alternative mRNA splicing or alternative protein processing events).

All publications and patent applications mentioned in this specification are herein incorporated by reference to the same extent as if each independent publication or patent application was specifically and individually indicated to be incorporated by reference.

The following examples are meant to illustrate, not limit, the invention.

EXAMPLES

Example 1

Materials and Methods

Animals. Adult male Wistar rats (250–275 g; Charles Rivers, Montreal) were housed 2 per cage in a temperature-controlled environment with a 12 hour light/12 hour dark cycle and were given free access to water and Purina laboratory chow. All animal procedures conformed to the *Guide for the Care and Use of Experimental Animals* endorsed by the Medical Research Council of Canada.

Tissue Preparation. Animals were anaesthetized with pentobarbital (100 mg/kg, i.p.) and perfused transcardially with 200 ml of saline (0.9%) followed by 150 ml of phosphate buffer (0.1 M) containing 4% paraformaldehyde. Brains were postfixed overnight and cryoprotected in phosphate buffer (0.01 M) containing 10% sucrose for two days. Sections 12 μm thick were cut from the appropriate brain region using a cryostat and processed for NAIP-LI.

Transient Forebrain Ischemia Model. Transient forebrain ischemia was performed using published modifications (Pulsinelli et al., 1982, supra) of the 4-VO method (Pulsinelli and Buchan, Stroke 19:913–914, 1988). Briefly, male Wistar rats (Charles River, St. Constant, Quebec, Canada) weighing 250 g were anaesthetized using 1.5% halothane. The alar foraminae of the first cervical vertebra were then approached through a dorsal midline neck incision. The vertebral arteries were permanently occluded by electrocautery. The carotid arteries were isolated through a ventral midline neck incision and silk ligatures were placed loosely around them. A silk suture was passed through the cervical region, posterior to the trachea, esophagus, external jugular veins, and common carotid arteries. The ends of the ligature were secured loosely to the nape of the neck with adhesive tape. The incisions were then closed with topical xylocaine jelly.

The following day, rats were randomly divided into two groups and subjected to either 10 min of forebrain ischemia (experimental) or manipulation without carotid occlusion (sham). Forebrain ischemia was achieved by lifting the common carotid arteries using the silk ligatures placed around them and occluding the vessels with micro aneurysm clips (#160–863, George Tiemann & Co., Plainview, N.Y.). The ligature encircling the neck muscles was then tightened in order to block any collateral circulation. Brain temperature was measured indirectly via a thermocouple probe placed in the temporalis muscle (Busto and Dietrich, J. Cerebral Blood Flow Metab 7:729–738, 1987). Body temperature was maintained between 36–37° C. by external warming. Ischemia was terminated by removal of the micro aneurysm clips and loosening of the neck ligature. Animals that convulsed during 4-VO, or following reperfusion, along with those that did not develop fully dilated pupils or loss of righting reflex during ischemia were omitted from the study.

Acute and chronic K252a administration we determined the effects of acute K252a (0.1 mg/kg, s.c.) administration on NAIP-LI in the hippocampus, thalamus and striatum. Two groups, composed of 3 animals each, were injected with K252a (0.1 mg/kg, s.c.) and allowed to survive for either 3 h or 24 h. A third group served as vehicle controls. These animals were injected with vehicle (1 ml/kg; aqueous solution containing 10% cyclodextrin and 0.5% DMSO) and sacrificed 3 hr later. To determine the effects of K252a on NAIP and NeuN levels we measured protein levels by Western blotting. Two groups, composed of 3 animals each, were injected with vehicle (1 ml/kg, s.c.) or K252a (0.1 mg/kg, s.c.) and killed 3 h later. We compared the effects of acute and chronic K252a administration on NAIP mRNA and protein levels in the hippocampus by in situ hybridization histochemistry and Western blotting, respectively. Three groups, composed of 6 animals each, were injected with vehicle (1 ml/kg, s.c.), K252a (0.1mg/kg, s.c.) or K252a (0.1 mg/kg, s.c., once daily for 7 days) and killed 3 h after the last injection. We examined the effects of K252a (0.1 mg/kg, s.c.) on blood pressure, gases ($O_2$ and $CO_2$) and pH in four animals. The femoral artery was cannulated with a polyethylene catheter for monitoring of blood pressure, gases and pH.

Effect of K252a administration on CA1 neuronal loss after transient global ischemia. Two groups, composed of 6 animals each, were injected subcutaneously (s.c.) with vehicle (1 ml/kg, s.c.) or K252a (0.1 mg/kg, s.c.) once daily for 7 days. All of the animals were subjected to 4-VO (10 min) 3 h after the last injection and given a second injection as soon as circulation was restored. A third group was injected with vehicle as described previously and subjected to sham 4-VO. Animals continued to receive either K252a (0.1 mg/kg, s.c.) or vehicle (1 ml/kg, s.c.) once daily for five days after the 4-VO or sham procedure. All of the animals were sacrificed 4 h after the last injection and brain samples processed for immunostaining of NeuN to assess cell loss in CA1.

Examination of the effects of virally-mediated NAIP overexpression on the loss of CA1 neurons produced by an episode of transient forebrain ischemia. Six male rats were stereotaxically injected with recombinant adenoviral constructs (pAdex1CAwt) containing either lacZ or myc-tagged NAIP into the left and right dorsal hippocampus, respectively. Adenovirus vectors (3 µl injected over 10 min; $1\times10^6$ particles $µl^{-1}$) were injected using a 28 gauge needle at the coordinates (in mm): AP −3.6, ML±2.2 and DV−3.2 from bregma[20]. Viral constructs have been previously described by Liston et al. (Nature 379:349, 1996). For construction of the adenovirus containing NAIP, a 3.7 kb BamHI fragment of NAIP was cloned in to the SwaI site of the adenovirus expression cosmid pAdex1CAwt, as described by Fujita et al. (J. Virol. 69:6180–6190, 1995). Seven days later, each of the animals were subjected to 10 minutes of 4-VO. All of the animals were sacrificed 5 days later. CA1 neuron loss was assessed histologically by counting NeuN immunoreactive neurons in the CA1 region of the hippocampus. A second group of 6 animals received unilateral injections of lacZ into the dorsal hippocampus. Neurons infected with lacZ and myc-tagged NAIP adenoviral constructs were identified by X-gal staining and immunohistochemical detection of the myc protein tag, respectively.

NAIP Riboprobe. The template for a rat NAIP riboprobe was generated by RT-PCR from rat hippocampal mRNA using primers directed against nucleotide sequences conserved in mouse and human NAIP[8]. A 227 bp sequence was ligated into the EcoR I site of the plasmid pcDNA3 (Invitrogen, Inc.). Both sense and antisense $^{35}$S-labelled riboprobes were generated from linearized plasmid templated using the MAXIscript In Vitro Transcription Kit (Ambion, Inc.). Specific activities ranged from $0.6–1.2\times10^8$ cpm/µl.

In Situ hybridization histochemistry. Cryostat sections (12 µm thick) were incubated in hybridization buffer containing either a sense or an antisense NAIP riboprobe ($1\times10^6$ cpm/100 µl/slide) overnight at 56° C. Sections were then treated with ribonuclease A (10 µg/ml) at 35° C. for 30 minutes and washed in 2×SSC for 30 minutes. After drying, the slides were dipped in Kodak NTB-2 emulsion (diluted 1:1 with distilled water) at 42° C., dried and exposed for 2 weeks at 4° C.

Polyclonal antisera and immunohistochemistry. An affinity-purified polyclonal antibody was used to detect NAIP-I. This antibody was raised in rabbits against Exons 7–11 of NAIP (150 amino acid fragment). Immunohistochemistry was performed using a standard procedure described previously by Robertson and Fibiger (Neuroscience 46:315–328, 1992). Briefly, sections (12 µm or 30 µm thick) were washed in 0.02 M phosphate buffered saline (PBS) containing 0.3% hydrogen peroxide for 10 min to block endogenous peroxidase activity. Sections were then washed three times in PBS and incubated in PBS containing 0.3% Triton X-100, 0.02% azide and NAIP primary antisera for NAIP (e.g., diluted 1:750 or 1:1000 or A60(1:1000)) for 48 hours. Next, the sections were washed 3 times with PBS and incubated with biotin-labelled donkey anti-rabbit secondary antisera (1:500) for 16 hours. The sections were then washed 3 times with PBS and incubated for 3 hours with PBS containing 0.3% Triton X-100 and streptavidin-horseradish peroxidase (1:100; Amersham). After 3 washes in PBS, the sections were rinsed in 0.1 M acetate buffer, pH 6.0. The reaction was visualized using a glucose oxidase-DAB-nickel method described previously (Shu et al., Neurosci. Lett. 85:169–171, 1988). The reaction was terminated by washing in acetate buffer, and the sections were mounted on chrom-alum coated slides. After drying, the sections were dehydrated through a graded series of alcohols, two changes of xylene, and coverslipped for microscopic observation. The antibody used for detection of ChAT-like immunoreactivity (ChAT-LI) was an affinity-purified goat antibody raised against human placenta ChAT (Chemicon International Inc.). Dopaminergic neurons in the midbrain were identified with a monoclonal antibody against TH (Incstar) while a monoclonal antibody against CaBP (Sigma) was used to localize Purkinje cells in the cerebellar cortex.

Double labelling immunohistofluorescence. Sections from the striatum, basal forebrain, brain stem and spinal cord were incubated with rabbit anti-NAIP (1:300) and anti-ChAT (1:500), ventral mesencephalic section were incubated with anti-NAIP (1:300) and anti-TH (1:500), and cerebellar sections with anti-NAIP (1:300) and anti-CaBP (1:500) for 48 hr at 4° C. in PBS containing 0.3% Triton X-100. Sections were rinsed in PBS and then incubated with a mixture of indocarbocyanine (Cy3)-labelled donkey anti-rabbit and the appropriate biotinylated secondary antisera (1:100 Amersham; 1:50 Amersham) prepared 24 hours prior to use. After 2 hr at room temperature and 1 hr at 37° C., sections were rinsed in PBS. Sections were then incubated for 3 hr at room temperature with streptavidin-fluoroisothiocyonate (FITC, 1:50 Amersham) in PBS not containing Triton X-100. Slides were coverslipped using a mounting medium of PBS containing phenylaminediamine (0.1 mM) and 90% glycerol and examined using a Zeiss Axioplan microscope equipped with both single and dual filter sets for the visualization of FITC and Cy3.

Tissue Preparation. Thalamus, hippocampus, striatum, and spinal cord were dissected on ice. First, each brain area (about 30 to 50 mg) was homogenized gently using a loose 2 ml-Dounce (type A, about 15 strokes) in 1 ml of sucrose buffer (0.25 M sucrose, 0.025 M NaCl, 1 mM EGTA and 15 mM Tris HCl pH 6.8). The buffer was also supplemented with 1 mM PMSF, 2 µg/ml of leupeptin and 5 µg/ml of aprotinin and kept on ice. Cell pellets were obtained upon centrifugation at 8000 g for 20 sec (Costar microfuge). Cells were resuspended in 0.4 to 0.7 ml of the same sucrose buffer described above and then disrupted using a motor driven Teflon pestle (Cole-Parmer instrument, settle at 2500 rpm) and a 2 ml tissue grinder (about 30 strokes). After a 10 min centrifugation at 13000 g (Denver instrument microfuge, 4° C.), the low speed supernatants were collected. Aliquots (10 µl) were pipetted for protein assay (Bio Rad). Purified low speed supernatants were then stored at −80° C. until further analysis.

SDS-PAGE, Electroblotting and Immunostaining. Tissue extracts (15–25 µg) were subjected to electrophoresis in a highly porous SDS-PAGE system (Doucet et al., 1990, 1993) which permits rapid and efficient transfer of proteins to a nitrocellulose membrane even when high molecular weight polypeptides are considered. The proteins resolved on 10% polyacrylamide, 0.1% bisacrylamide running gels (length fixed to 5.5 cm) were transferred to nitrocellulose sheets electrophoretically as described by Towbin et al. (1979) with the exception that methanol was omitted in the transfer buffer. The nitrocellulose membranes were first incubated in Tris-HCl saline buffer pH 7.2 (TBS) containing 5% blotto for 1 hr at room temperature plus 1 hr at 42° C.

The nitrocellulose membranes were then incubated for 1 hr in 1% blotto at room temperature with one of the following antibodies: NAIP (1:1000) and A60 (1:1000; generously provided by Dr. R. J. Mullen). Blots were then washed in TBS-tween (5 washes, 3 min each) and incubated for 1 hr in 1% blotto containing a highly purified biotin-conjugated anti-rabbit (1:2000; Bio/Can Scientific) or anti-mouse antibody (1:2000; Bio/Can Scientific). Blots were again washed as before and incubated for 1 hr with streptavidin-horseradish peroxidase (1:2000, Amersham). Finally, the blots were developed by enhanced chemiluminescense (ECL, Amersham). Preparation of 6-OHDA lesion rodents. Male Wistar rats (250–300 g; n—6 per group) were stereotaxically injected with recombinant adenoviral constructs containing either myc-tagged NAIP (3 $\mu$l; 1×10$^6$ particles per microliter) or the bacterial gene lacZ (3 $\mu$l; 1×10$^6$ particles per microliter) into the right dorsolateral striatum. The adenoviral constructs are taken up by dopaminergic terminals in the striatum and transported to cell bodies located in the SNC (Ridoux et al., 1994). One week later, all animals received a single stereotaxic injection of 6-OHDA (3 $\mu$l; 20 $\mu$g/ml) into the right striatum at the same coordinates as the preceding adenoviral injection. After three weeks recovery, all animals of the animals were intracardially perfused with saline followed by fixative and brains sectioned for immunohistochemical detection of tyrosine hydroxylase; the neuronal specific marker, NeuN. and Myc, the protein marker of the NAIP adenoviral construct. Facial Neuron Axotomy: The left facial nerve was transected and the animals were killed 1, 3, 7, or 14 days later. The fresh brainstem were removed and the right and left facial nuclei micro dissected as described previously (Tetzlaff et al., J. Neurosci. 8:3181–3189, 1988). Total RNA was extracted, reverse transcribed and amplified using specific PCR primers to NAIP and XIAP based on the rat sequence information provided by Apoptogen. Ser. dilutions of the RT-product (cDNA; 3, 6, 12, and 24 ng) were used at different cycle number of amplification in order to ensure linearity of the amplification. Phosphoimaging was used to quantify the amplification products. The specificity of the PCR products was confirmed by Southern blotting using a 50 mer oligonucleotide probe. Amplification of cyclophilin was used to confirm equal amounts and quality of input RNA. Effects of axotomy on NAIP, XIAP and HIAP-2 expression in adult rats was also examined by in situ hybridization histochemistry.

Testing for Specificity of NAIP Antisera. The specificity of NAIP antisera was assessed by both immunohistochemistry and Western blotting. In this study, we determined whether preabsorption of the antisera with glutathione-S-transferase (GST)-NAIP fusion protein eliminated NAIP-LI. In a second experiment, immunohistochemical localization of NAIP-LI was examined in coronal sections cut from a variety of levels in the forebrain, midbrain, hindbrain and spinal cord. In a third experiment, double immunofluorescence labelling was performed using antibodies against NAIP and several marker proteins which included choline acetyltransferase (ChAT), tyrosine hydroxylase (TH), and calbindin D-28K (CaBP) to examine the localization of NAIP-LI in cholinergic, dopaminergic and Purkinje neurons, respectively.

Statistical analysis. A one-way analysis of variance was performed on the cell count and densitometric data. A one-way analysis of variance with repeated measures over time was conducted on the blood gases and pH. If the analysis was significant, multiple comparisons were performed using the Newman-Keuls test. An unpaired student t-test was performed on the cell count data for the adenoviral experiment.

Example 2

Distribution of NAIP-like Immunoreactivity in the Central Nervous System

The affinity purified NAIP antibody recognized a single band at 150 kD, which corresponds to the predicted molecular weight for NAIP. In contrast, antisera that had been preabsorbed with NAIP fusion protein failed to detect this band. Neuronal labelling was detected by immunohistochemistry with the affinity purified antibody. This labelling was eliminated by preabsorption of the antisera with GST-NAIP fusion protein (data not shown). These results indicate that this antibody selectively recognizes NAIP.

1. Telencephalon.

Figure 12A:
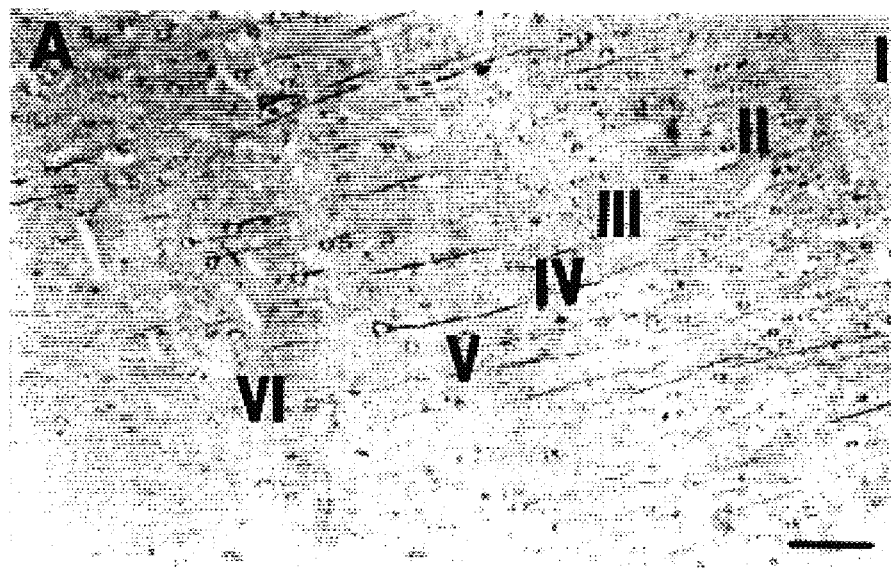
FIGS. 12A and 12B are photographs showing NAIP-like immunoreactivity (NAIP-LI) in the neocortex. Neuronal perikarya and processes were moderately labelled in all cortical layers (A). NAIP-LI in a layer V pyramidal neuron, note intense labelling in the apical dendrite (arrow) (B). Scale bars=300 μm (A); 30 μm (B).
Figure 12B:

Cortex. Neurons which displayed NAIP-LI were observed in all layers of the neocortex (II–VI) (FIG. 12A). Low to moderate levels of NAIP-LI were detected in all cortical regions examined. Immunoreactive labelling in the cell body was moderate and confined to the cytoplasm. By comparison, dendritic staining was more intense with the most prominent labelling observed in the apical dendrites of layer V pyramidal neurons (FIG. 12B).

Figure 13A:
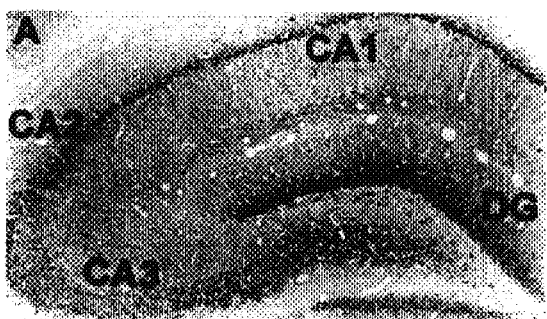
FIGS. 13A–13D are photographs showing NAIP-LI in the hippocampus. NAIP-LI was detected in pyramidal neurons (CA1–CA3), dentate granule cells (DG) and interneurons (A). Within the CA1 subfield, NAIP-LI was present in the cell bodies and dendrites of pyramidal neurons (B). The intensity of NAIP-LI exhibited by neurons in CA1–CA3 subfields and dentate gyrus appeared similar (B, C and D). By comparison to these neuronal populations, more intense staining was apparent in interneurons scattered throughout the hippocampus in stratum oriens, lucunosum of CA1 (B), lucidum of CA2 and CA3 (C), and the dentate hilus (D). Arrow heads indicate interneurons. Scale bars=500 μm (A); 300 μm (B, C, D).
Figure 13B:
Figure 13C:
Figure 13D:
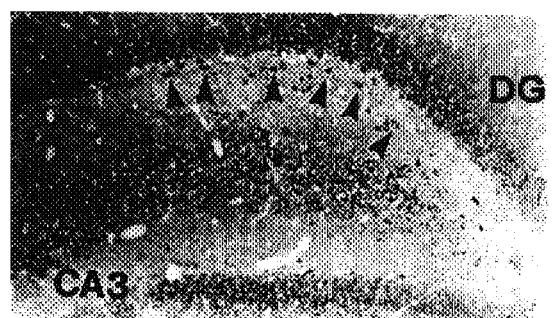

Hippocampus. In the hippocampus, all of the pyramidal neurons in CA1–CA3 subfields as well as granule cells in the dentate gyrus displayed moderate levels of immunoreactivity that was apparent in both perikarya and processes (FIGS. 2, 13A, 13B, 13C). Interneurons scattered throughout the hippocampus in the oriens layer, stratum radiatum and lucunosum moleculare of CA1 as well as stratum lucidum of CA2 and CA3 displayed intense labelling (FIGS. 13B, 13C, 13D).

Figure 14A:
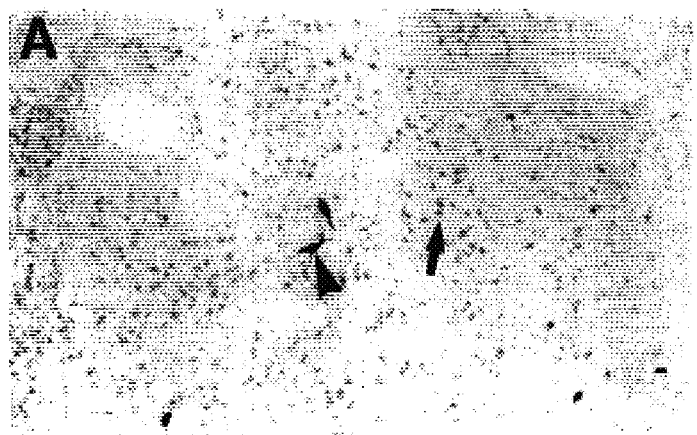
FIGS. 14A–14C are photographs showing NAIP-LI in the striatum and double-labelling immunohistofluorescence of striatal neurons for NAIP and choline acetyltransferase (ChAT). Large neurons which displayed intense labelling were observed throughout the caudate-putamen (arrow heads) (A). By contrast, medium-sized neurons were weakly labelled with the NAIP antibody (arrow) (A). Double-labelling immunofluorescence showing a perfect overlap between NAIP-LI (B) and ChAT-immunoreactive neurons (C) (arrowheads). Scale bars=300 μm (A); 30 μm (B, C).
Figure 14B:
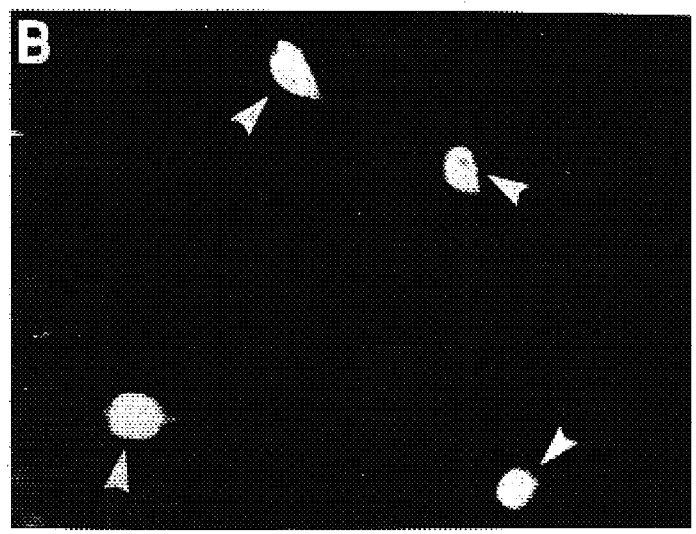
Figure 14C:
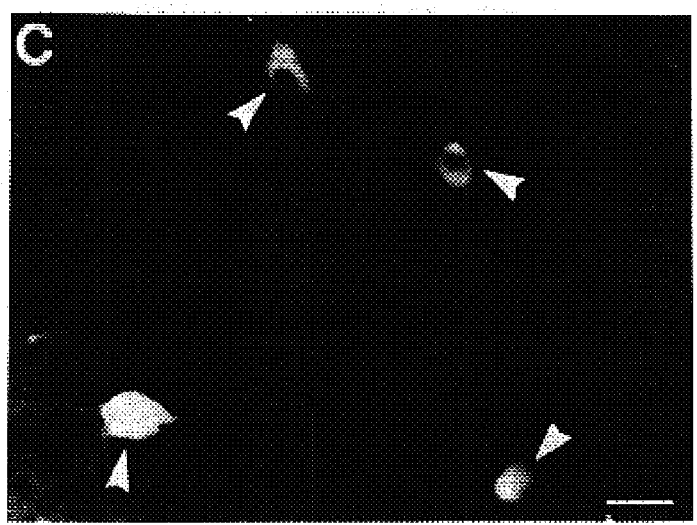

Striatum. Strongly labelled neurons were observed in the caudate-putamen and nucleus accumbens. These immunoreactive neurons were large (25–30$\mu$m) and represented a very small proportion, approximately 1%, of the total striatal neuron population (FIG. 14A). Consistent with these findings, double labelling with ChAT antisera revealed that NAIP-LI was localized exclusively in cholinergic interneurons (FIGS. 14B, 14C). All of the other neurons in this structure exhibited very low levels of NAIP-LI.

Figure 15A:
FIGS. 15A–15C are photographs showing NAIP-LI in output structures of the basal ganglia. Labelled neurons were observed in the globus pallidus (A), endopeduncular nucleus (B) and substantia nigra (C). In these structures, especially the interpeduncular nucleus, strongly labelled fibers were also seen (B). In the substantia nigra, NAIP positive neurons were located predominantly in substantia nigra pars compacta (SNC). Scattered immunoreactive neurons were also present in the substantia nigra pars reticulata (SNR) and substantia nigra pars lateralis (SNL). Dendrites originating from the pars compacta were observed extending ventrally into the SNR (C). Scale bar=300 μm.

Globus Pallidus. Large, intensely stained bipolar neurons were observed in this striatal projection site (FIG. 15A).

Figure 16A:
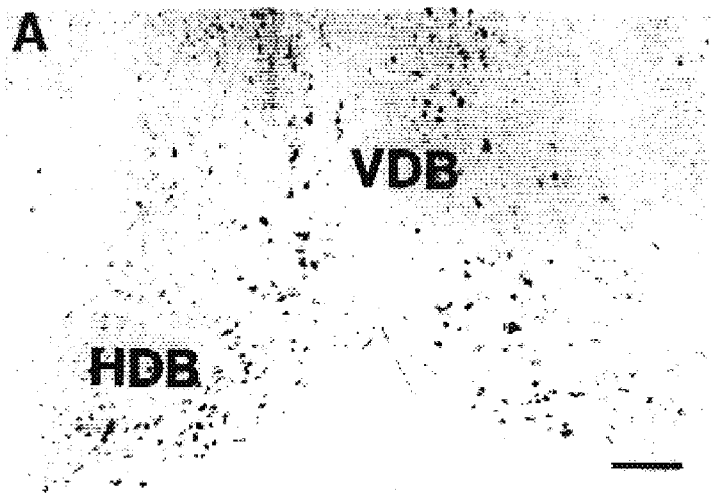
FIGS. 16A–16C are photographs showing NAIP-LI in the diagonal band and double-labelling immunohistofluorescence of diagonal band neurons for NAIP and ChAT. NAIP-immunoreactive neurons were present in the horizontal as well as the vertical limb of the diagonal band (A). Double-labelling revealed little overlap between NAIP (B) and ChAT positive neurons (C) in the diagonal band. Arrows indicate a single double-labelled neuron. Scale bars=300 μm (A); 30 μm (B, C).
Figure 16B:
Figure 16C:
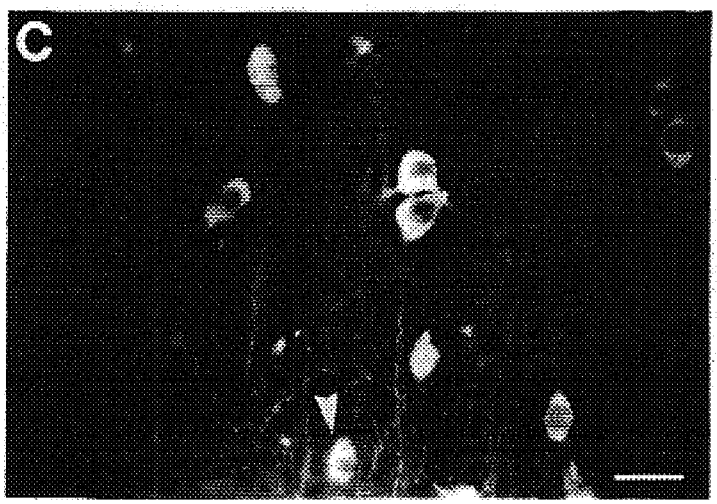

Basal forebrain. Moderately immunoreactive neurons were detected in both the horizontal and ventral limbs of the diagonal band of Broca as well as the medial septal nucleus and ventral pallidum (FIG. 16A). The distribution of these NAIP immunoreactive cell bodies appeared to match the distribution of cholinergic neurons in the basal forebrain. However, double labelling for NAIP and ChAT revealed little colocalization of NAIP- and ChAT-LI in the medial septum and diagonal band (FIGS. 16B, 16C).

2. Diencephalon.

Figure 17A:
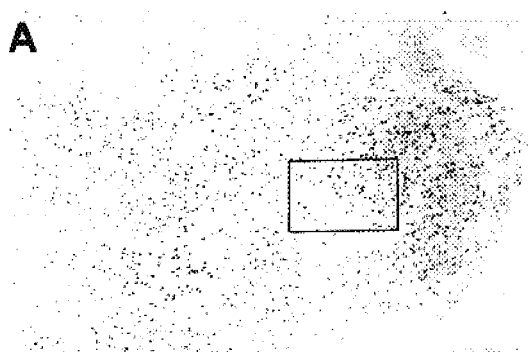
FIGS. 17A–17D are photographs showing NAIP-LI in the diencephalon. NAIP-LI was detected in nearly all thalamic areas with more intensely labelled neurons apparent in the ventromedial and ventral posterior nuclei (A). Higher magnification of the squared area indicated in (A) showing labelled neurons in the ventral posterior nucleus (B). In the habenula, NAIP-LI was displayed by both medial and lateral habenular nuclei. A small population of large bipolar neurons in the lateral hebenula exhibited very strong NAIP-LI (C). In the hypothalamus, NAIP-LI was rarely detected (D). Scale bars=600 μm (A); 300 μm (C, D).
Figure 17B:

Thalamus. Moderate to high intensity labelling was observed in a large number of medium-sized neurons situated in ventral and lateral portions of the thalamus (FIGS. 17A, 17B). Although fewer in number, immunoreactive neurons were also detected in anterior, intralaminar and medial aspects of the thalamus.

Figure 17C:

Habenula. Numerous small, round, moderately immunoreactive perikarya were seen in the medial habenular nucleus. In the lateral habenular nucleus, a few intensely stained neurons of medium size were detected (FIG. 17C).

Figure 17D:
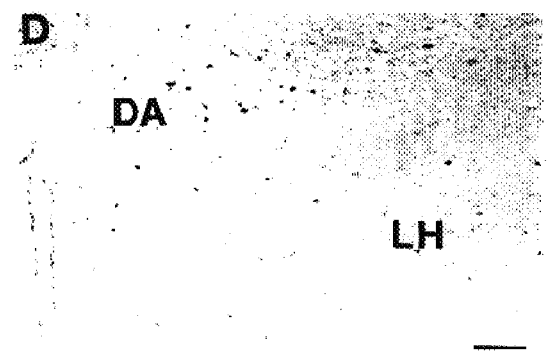

Hypothalamus. In comparison to the thalamus, little NAIP-LI was seen in the hypothalamus. A small number of weakly stained neurons were detected in the arcuate nucleus as well as dorsal and lateral hypothalamic areas (FIG. 17D).

Figure 15B:

Entopeduncular Nucleus. Intense labelling was observed in this basal ganglia output. In addition to perikarya, NAIP-LI was highly enriched in neuronal processes that formed a fibrous network (FIG. 15B).

3. Mesencephalon.

Figure 15C:
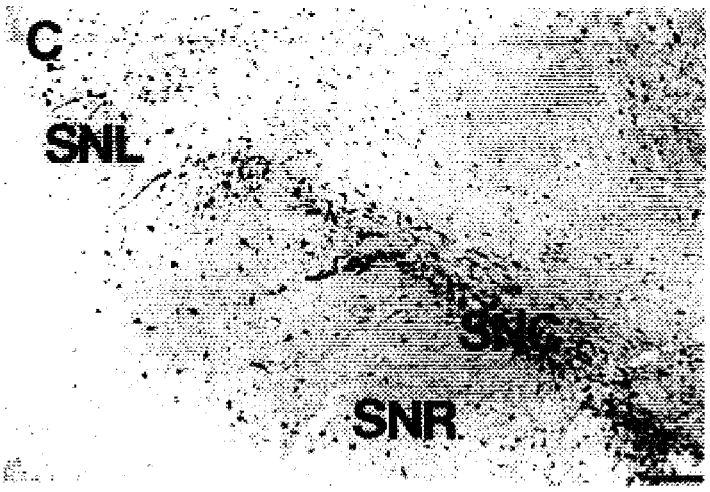
Figure 18A:
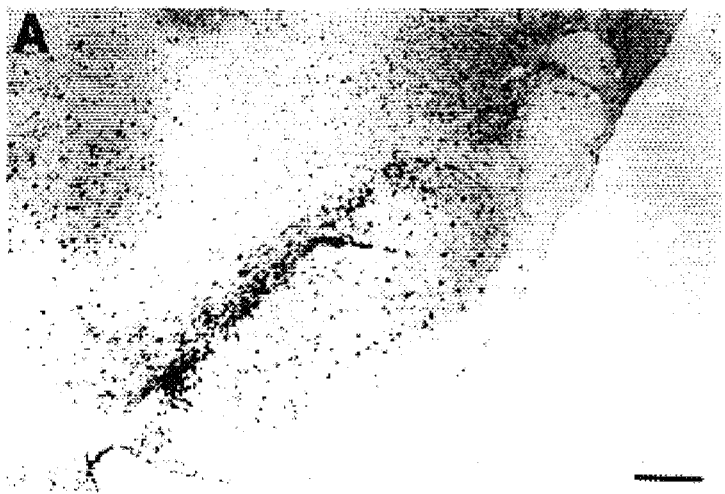
FIGS. 18A–18C are photographs showing NAIP-LI in the substantia nigra and double-labelling of nigral neurons for NAIP and TH. NAIP-LI was displayed chiefly by neurons in the SNC (A). Double-labelling of SNC neurons for NAIP (B) and tyrosine hydroxylase (C) showing the high cellular overlap of these two markers (arrowheads). Scale bars=500 μm (A); 30 μm (C).
Figure 18B:
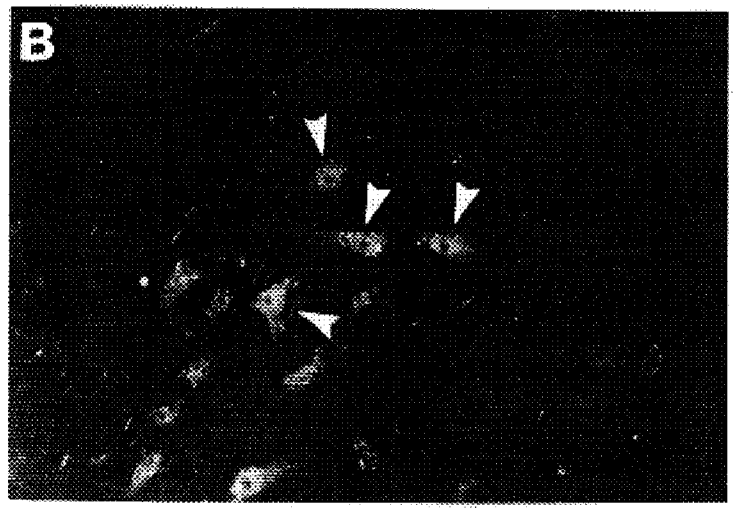
Figure 18C:
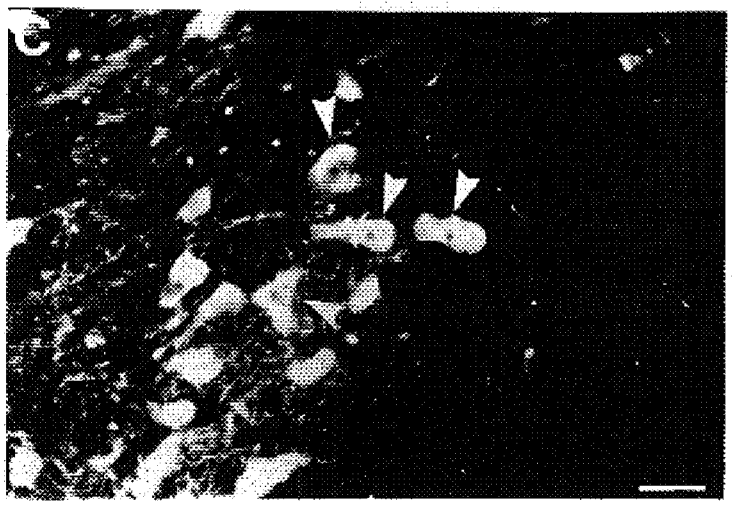
Figure 19A:
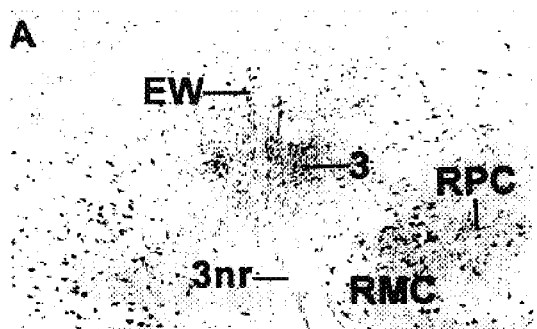
FIGS. 19A–19D are photographs showing NAIP-LI in cranial nerve and relay nuclei of the brain stem. Intense NAIP-LI was detected in several cranial nerve nuclei such as the oculomotor and Edinger-Westphal nucleus (A), trigeminal and cochlear (B), facial (C), vagus and hypoglossal nucleus (D). Strong labelling of the nerve roots extending ventrally from the oculomotor and cochlear nerve is apparent (A and B). NAIP positive neurons were also observed in brain stem relay nuclei such as the red (A) as well as gracile and cuneate nucleus (D). Scale bar=400 µm.
Figure 20A:
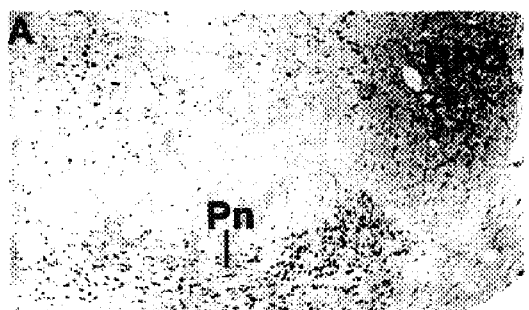
FIGS. 20A–20D are photographs showing NAIP-LI in relay and reticular nuclei of the brain stem and cerebellum. NAIP-LI was observed in a large number of neurons in the pontine nucleus and rostral periolivary area (A). The locus coeruleus as well as the three major nuclei of the trigeminal nerve: mesencephalic, principal sensory and motor nucleus also displayed intense NAIP-LI (B). Neurons in the gigantocellular reticular nucleus were strongly labelled (arrowheads indicated giant-sized neurons) (C) and vestibular nucleus (D). Intense NAIP-LI was also present in cerebellar nuclei such as lateral and interposed cerebellar nucleus (D). Scale bar=400 µm.
Figure 21A:
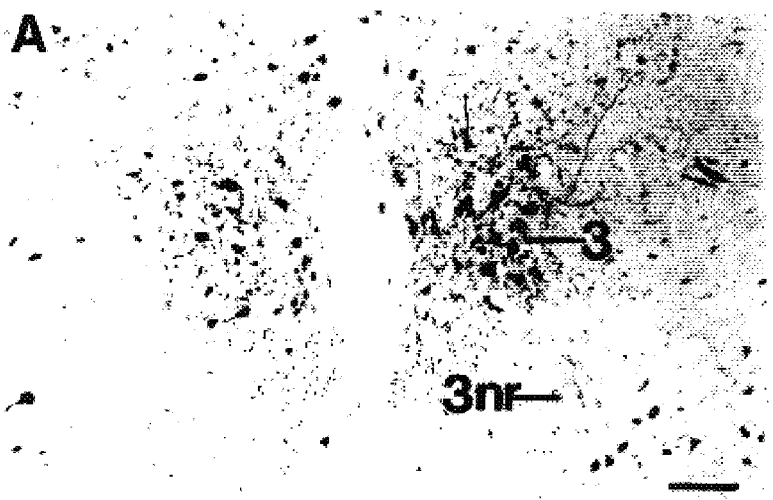
FIGS. 21A–21C are photographs showing NAIP-LI in the oculomotor nucleus and double-labelling immunohistofluorescence of oculomotor neurons for NAIP and ChAT. Example of NAIP-LI in the oculomotor nerve showing cell body and axonal labelling (A). Immunohistofluorescence labelling of NAIP in the oculomotor nucleus (B). Immunohistofluorescence labelling for ChAT (C) in the same region of the oculomotor nucleus shown in (B). Arrows heads indicate double labelled neurons while arrows show examples of NAIP immunoreactive neurons which do not contain CHAT. Scale bars=300 µm; 30 µm (B, C).

In the substantia nigra, the majority of NAIP-LI neurons were located in the substantia nigra pars compacta. NAIP-LI was also present within the dendrites of these neurons which extend ventrally into the substantia nigra pars reticulata (FIG. 15C). A few NAIP-LI neurons were observed in the substantia nigra pars reticulata and pars lateralis (FIGS. 15C, 18A). Double labelling revealed that the majority of neurons which displayed NAIP-LI in these regions were dopaminergic (FIGS. 18B, 18C). The most intensely labelled neurons in the midbrain were located in the oculomotor nucleus. Strongly labelled fibers were also apparent in the oculomotor nerve root (FIGS. 9A, 21A). High levels of NAIP-LI were detected in neurons of the Edinger-Westphal nucleus and trochlear nuclei (FIG. 19A). Both the parvocellular and magnocellular parts of the red nucleus displayed intense NAIP-LI (FIG. 19A). In the pontine nucleus, numerous small round perikarya were observed (FIG. 20A).

4. Met- and mylencephalon.

Figure 19B:
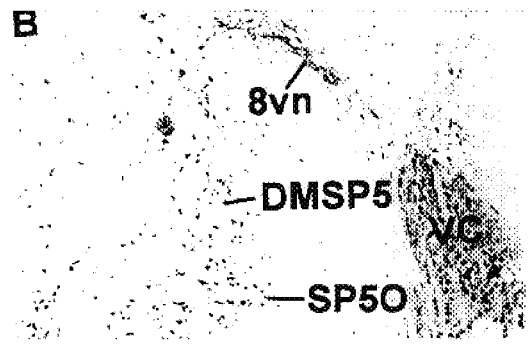
Figure 19C:
Figure 19D:
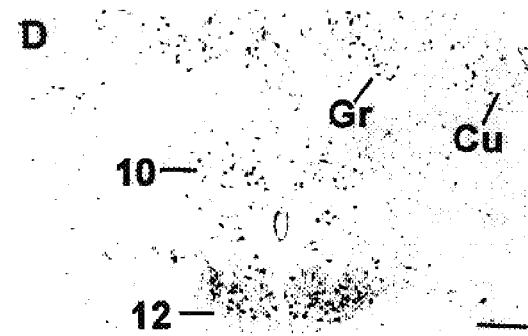
Figure 20B:
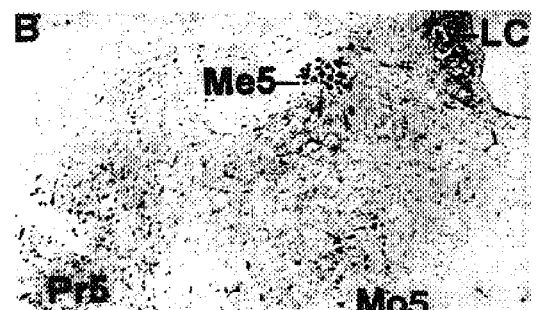
Figure 20C:
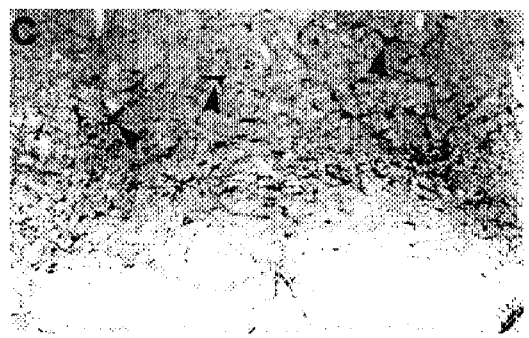
Figure 21B:
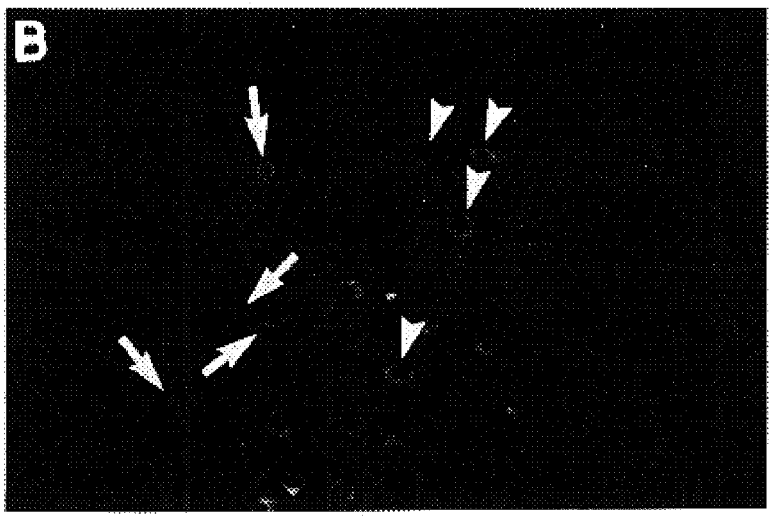
Figure 21C:
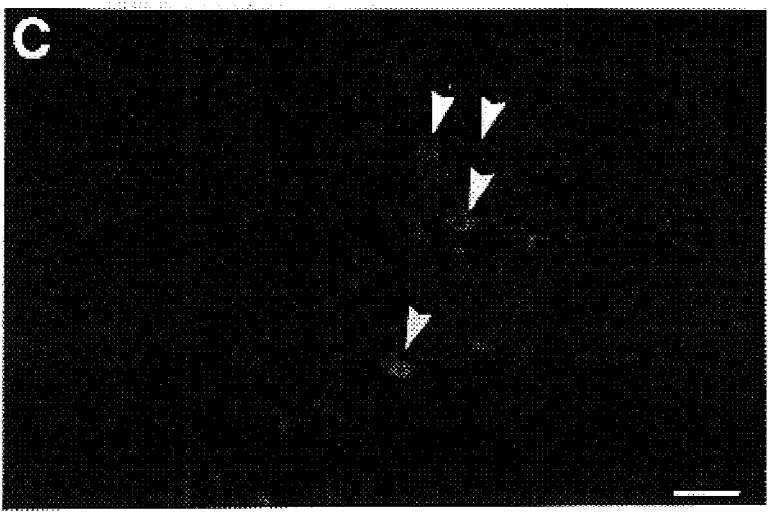

Brainstem. The majority of cranial nerve nuclei in the brainstem displayed strong NAIP-LI. Intensely NAIP positive neurons were present in all the major nuclei of the trigeminal nerve. These included the spinal, mesencephalic, principal sensory and motor nuclei of the trigeminal nerve (FIGS. 19B, 19C, 20B). The strongest labelling was displayed by medium-sized neurons in the mesencephalic trigeminal nucleus (FIG. 20B). Intense NAIP-LI was also detected in the vestibular nucleus, cochlear nucleus and nerve fibers of the vestibulocochlear nerve (FIGS. 19B, 19D). Other cranial nerve nuclei which contained prominent labelling included the facial nucleus, nucleus of the solitary tract, motor nucleus of vagus and hypoglossal nucleus (FIGS. 19C, 19D). Double labelling of the cranial nerve nuclei for NAIP and ChAT revealed that in motor nuclei such as the oculomotor nucleus, the majority of NAIP positive neurons were also immunoreactive for ChAT (FIGS. 21B, 21C). Neurons located within brain stem relay nuclei such as the gracile nucleus, cuneate nucleus, gigantocellular nucleus and locus coeruleus were also strongly stained with the NAIP antibody (FIGS. 19D, 20B, 20C). In addition, NAIP-LI was detected in the trochlear nucleus, nucleus ambiguus, interpenduncular nucleus, inferior olivary nucleus and lateral reticular nucleus.

Figure 20D:
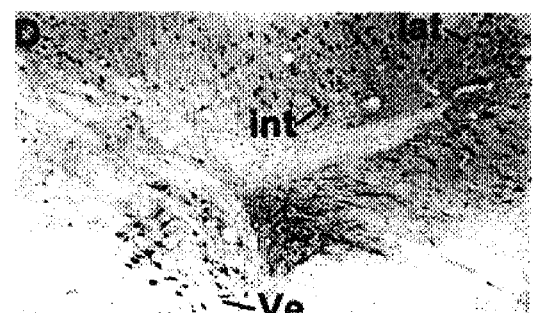
Figure 22A:
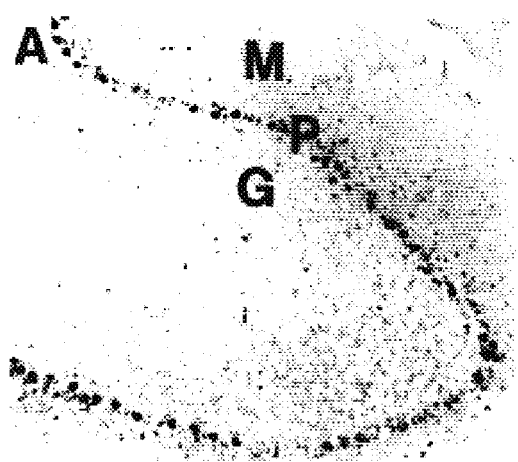
FIGS. 22A–22C are photographs showing NAIP-LI in the cerebellar cortex. NAIP positive somata with an orderly monolayer alignment were detected in the cerebellar cortex (A). NAIP-LI was not observed in any other layers (A). Immunohistofluorescence labelling of NAIP in the cerebellar cortex (B). Immunohistofluorescence labelling of calcium binding protein (28 kD, CaBP) showing Purkinje cells (C) in the same region of the cerebellum as (B). Note the perfect overlap between neurons immunoreactive for NAIP (B) and CaBP (C). Scale bars=300 µm(A); 30 µm (B, C).
Figure 22B:
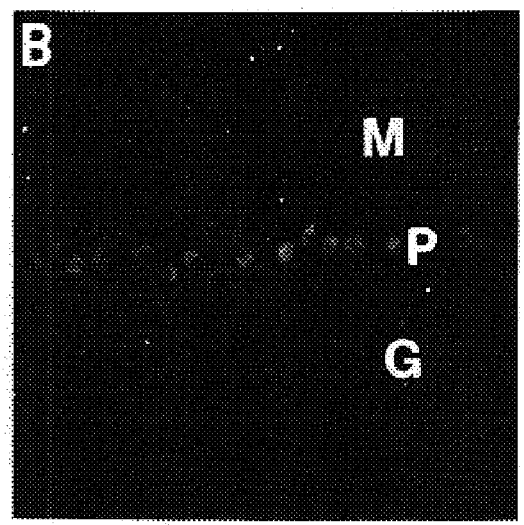
Figure 22C:
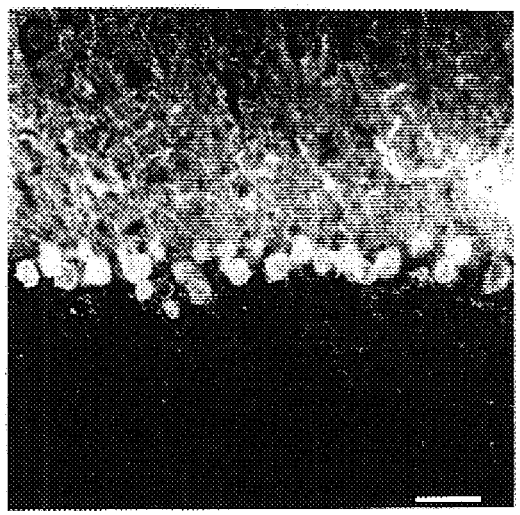
Figure 23A:
FIGS. 23A–23D are photographs showing NAIP-LI in the spinal cord. Numerous NAIP positive perikaya, varying in size and morphology, were observed at the cervical (A), thoracic (B, C) and sacral (D) levels of the spinal cord. Intensely labelled neurons are located predominantly in the anterior part of the spinal cord. Note that NAIP-LI in present within neuronal processes in both gray and white matter. Scale bar=400 µm.
Figure 23B:
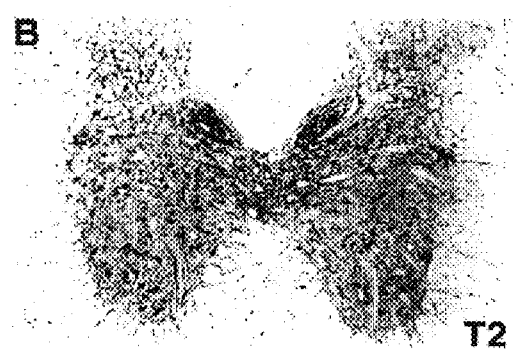
Figure 23C:
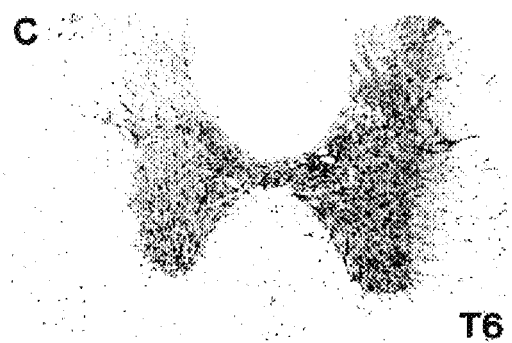
Figure 23D:
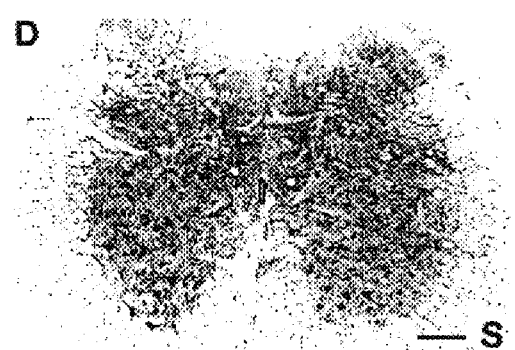

Cerebellum. In the cerebellum, NAIP-LI perikarya, round in shape, were observed in a single layer of the cerebellar cortex (FIG. 22A). Double immunofluorescence labelling of these neurons with an antibody raised against calbindin D-28K, a marker protein for Purkinje cells, indicated that NAIP-LI was located in Purkinje cells (FIGS. 22B, 22C). NAIP-LI was not detected in any other layer of the cerebellar cortex. Cell bodies containing NAIP-LI were also observed in deep cerebellar nuclei such as the interposed and lateral nuclei (FIG. 20D).

5. Spinal Cord.

Figure 24A:
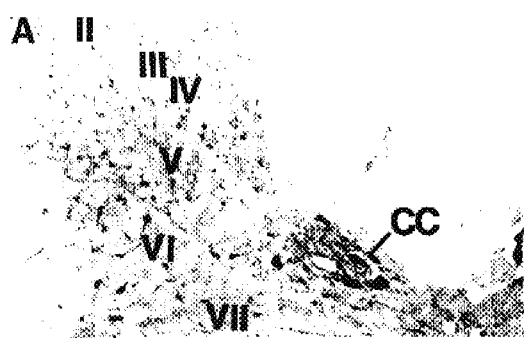
FIGS. 24A–24D are photograph showing distribution of NAIP-LI in the dorsal and ventral horns of the spinal cord at thoracic level 2. NAIP positive neurons are concentrated within the ventral horn (laminae 7, 8 and 9) and Clarke's column (lamina 7). The majority of NAIP positive perikarya in the ventral horn were large and triangular (arrowheads). NAIP positive perikarya, though fewer in number and smaller in size, were also seen in laminae V and VI. Laminae I-IV contained few immunoreactive neurons (A). Immunohistofluorescence labelling for NAIP in the ventral horn of the spinal cord (B). Immunohistofluorescence labelling for ChAT (D) in same region of the ventral horn of the spinal cord shown in (C). Arrowheads indicate double labelled neurons. Scale bars=300 µm (A, B); 30 µm (C, D).
Figure 24B:
Figure 24C:
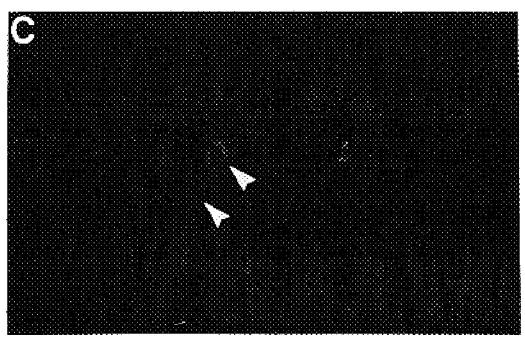
Figure 24D:
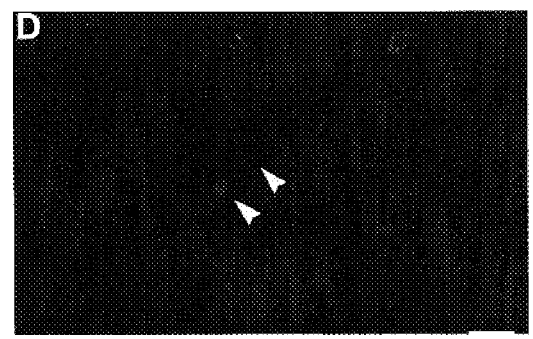

Intensely labelled perikarya which varied in size and morphology were observed at various levels of the spinal cord, located primarily in the ventral horn (laminae VIII and IX) and intermediate zone (lamina VII) (FIGS. 23, 24A, 24B). The most prominently labelled cells in the ventral horn were very large neurons, presumably cc-motor neurons (FIG. 24B). In keeping with this proposal, these neurons were double labelled with the CHAT antibody (FIGS. 24C, 24D). Large perikarya were also observed in lamina VII, particularly in close proximity to the central canal. Clarke's column, located in lamina VII, was strongly labelled with the NAIP antibody. A small number of neurons were detected in laminae V and VI of the dorsal horn. A few positive neurons with small round perikarya were also observed in the dorsal horn (laminae I–IV) (FIG. 24A). Lastly, fiber staining was present within white matter of the spinal cord (FIG. 23).

Example 3

Effect of Transient Forebrain Ischemia on Levels of NAIP mRNA in the Hippocampus Five groups, consisting of 4 animals each, were subjected to 10 min of four-vessel occlusion (4-VO) and anaesthetized with pentobarbital (100 mg/kg, i.p.) 2, 12, 24, 48 and 72 h following recirculation. A sixth group, containing 4 animals, served as controls. These animals were anaesthetized with pentobarbital (100 mg/kg, i.p.) 48 h after the sham 4-VO procedure. Once deeply anesthetized, all of the animals were killed by cervical decapitation. The brains were rapidly removed, frozen in isopentane (−65° C.) and sections 12 $\mu$m thick cut through the dorsal hippocampus using a cryostat. NAIP mRNA was detected in hippocampal sections by in situ hybridization histochemistry.

Basal expression of NAIP mRNA was only detectable in the dentate gyrus (FIG. 1). Following transient cerebral ischemia, increases in NAIP mRNA levels were first observed in the CA1 region at 24 h. The hybridization signal for NAIP continued to increases at 48 h and peaked at 72 h. Unlike CA1 pyramidal neurons, dentate granule cells and CA3 neurons displayed only modest increases in NAIP levels 24, 48, and 72 h after four-vessel occlusion (4-VO).

Example 4

Virally-mediated NAIP Overexpression Blocks Nigrostriatal Pathway Degeneration Following Intrastriatal 6-OHDA Lesion Injection of 6-hydroxydopamine into the rodent striatum produces a delayed degeneration of the nigrostriatal pathway. We have previously shown that overexpression of the novel antiapoptotic protein NAIP, reduces the loss of hippocampal neurons produced by a brief episode of cerebral ischemia. In the present study, we demonstrate that virally-mediated overexpression of NAIP also attenuates nigrostriatal damage in the 6-OHDA model of Parkinson's disease.

Figure 25:
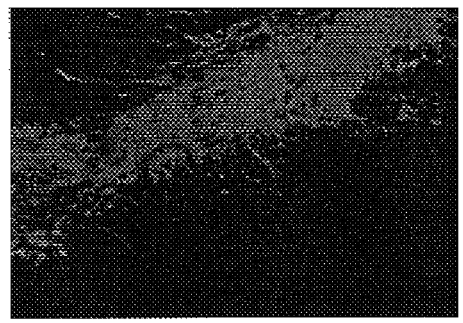
FIG. 25 is a photograph showing the effects of adenovirally mediated NAIP overexpression on nigral TH—immunoreactivity following striatal 6-OHDA. Top: Control; Middle: Lac7-6-OHDA; Bottom: NAIP-6-OHDA.
Figure 25:
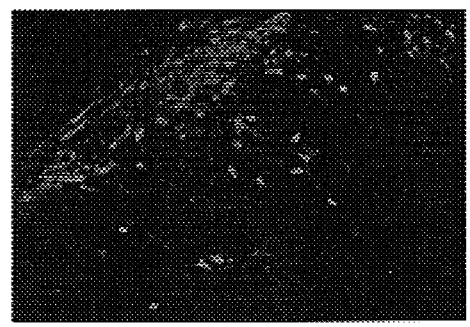
Figure 25:
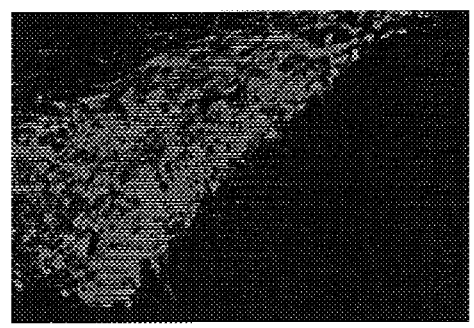

Instriatal injection 6-OHDA resulted in a significant reduction of dopamine neurons labelled with the antibody against tyrosine hydroxylase (FIG. 25—top and middle panels). Preliminary results indicate that the NAIP adenoviral construct significantly reduced the loss of dopamine neurons produced by intrastriatal administration of 6-hydroxydopamine (FIG. 25; middle and bottom panel).

The ability of the NAIP adenoviral vector to reduce dopamine neuron loss produced by 6-hydroxydopamine suggests that treatments capable of increasing NAIP expression may have utility in the treatment of Parkinson's disease.

Example 5

Effects of Transient Forebrain Ischemia on NAIP-like Immunoreactivity in the Hippocampus, Striatum and Thalamus Three groups, composed of 5 animals each, were subjected to 10 min of four-vessel occlusion (4-VO) and anaesthetized with pentobarbital (100 mg/kg, i.p.) 3, 24, and 72 h following reperfusion. A fourth group, containing 4 animals, served as controls. These animals were anaesthetized with pentobarbital (100 mg/kg, i.p.) 24 h after the sham 4-VO procedure. Once deeply anesthetized, all animals were perfused transcardially with 200 ml of saline (0.9%) followed by 150 ml of phosphate buffer (0.1 M) containing 4% paraformaldehyde. Brains were postfixed overnight and cryoprotected in phosphate buffer (0.01 M) containing 10% sucrose for two days. Sections 12 μm thick were cut from the appropriate forebrain region using a cryostat and processed for NAIP-I. A third experiment was performed utilizing double-labelling immunohistofluorescence to determine if striatal NAIP-I was co-localized in neurons that express the cholinergic marker enzyme, choline acetyltransferase (ChAT).

Figure 3A:
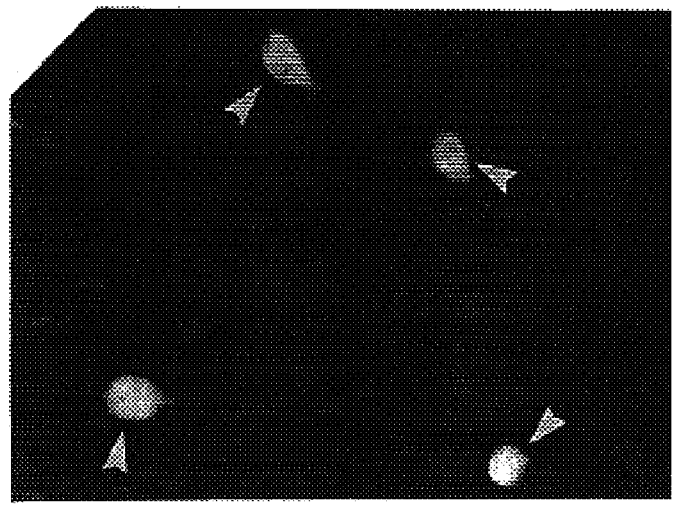
FIGS. 3A and 3B are photographs showing double labelling immunohistofluorescence of striatal neurons for NAIP-like (A) and choline acetyltransferase (ChAT; B) immunoreactivity. Overlap between neurons that display NAIP-like and ChAT immunoreactivity (arrows) indicates that, in the striatum, NAIP is located exclusively in cholinergic neurons. Scale bar=40 μm.
Figure 3B:
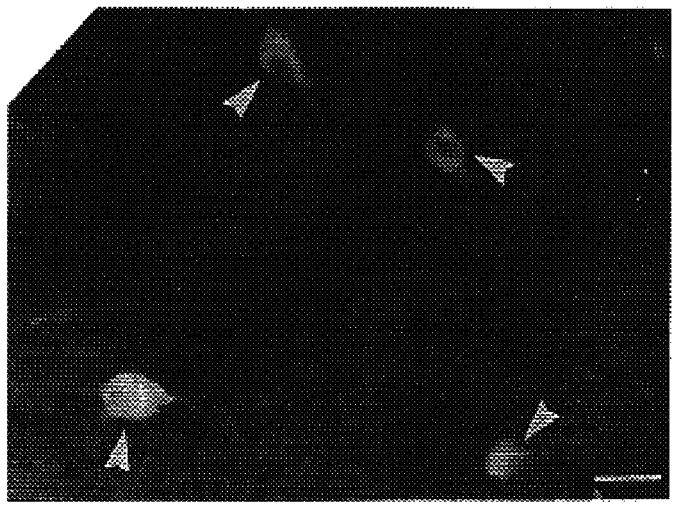

Consistent with the in situ hybridization histochemistry results, low-moderate levels of NAIP-I were detected in hippocampal CA1 neurons of untreated animals (FIG. 2). Similarly, the intensity of NAIP-I in CA1 neurons did not appear to be altered 3 h after 10 min of transient forebrain ischemia. However, in contrast to NAIP mRNA levels, NAIP-I decreased to below basal levels 24 h and 72 h following recirculation. NAIP-I in the striatum was located in about 1% of the total neuronal population. These neurons were large in size (25–30 μm diameter) and displayed higher levels of NAIP-I than hippocampal CA1 neurons. Double labelling immunohistofluorescence revealed that striatal NAIP-I was localized in neurons that contained ChAT immunoreactivity (FIG. 3). Transient forebrain ischemia produced a large elevation in NAIP-I in these striatal neurons 3 h after reperfusion (FIG. 2). NAIP-I still appeared to be elevated at 24 h but had returned to basal levels 72 h after 4-VO. The majority of neurons in the ventral-lateral and ventral-medial portions of the thalamus contained NAIP-I (FIG. 2).

These neurons displayed large increases in NAIP-I 3 h after restoration of blood flow. NAIP-I still appeared to be elevated at 24 h but returned to basal levels 72 h after reperfusion.

Example 6

Effects of Acute K252a Administration on NAIP Levels

Figure 29:
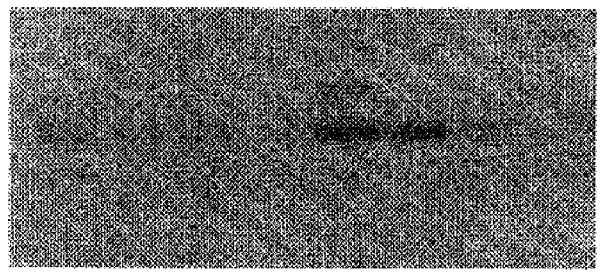
FIG. 29 is a photograph showing NAIP expression in axotomized and control newborn cells.
Figure 29:
Figure 30A:
FIGS. 30A–30I are photographs showing the effects of a single administration of vehicle (1 ml/kg, s.c.) or K252a (0.1 mg/kg, s.c.) on NAIP-like immunoreactivity in the hippocampus (A, D and G) thalamus (B, E and H) and striatum (C, F and I). In animals treated with vehicle, moderate levels of NAIP-like immunoreactivity were present in hippocampal CA1 (CA1; A) and thalamic (THAL; B) neurons. In striatum, high levels of NAIP-like immunoreactivity were exhibited by cholinergic neurons (arrow head) (C). NAIP-like immunoreactivity was elevated in all three regions 3 h after administration of K252a (0.1 mg/kg, s.c.) (D, E and F). In striatum, K252a appeared to elevate NAIP-like immunoreactivity primarily in medium-sized neurons (arrows) (F). By 24 hours, NAIP-like immunoreactivity had returned to basal levels in the hippocampus (G), thalamus (H) and striatum (I). Scale bars=300 µm (A, B, D, E, G, and H); 50 µm (C, F, and I).
Figure 30B:
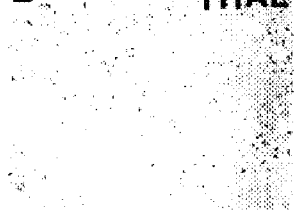
Figure 30C:
Figure 30D:
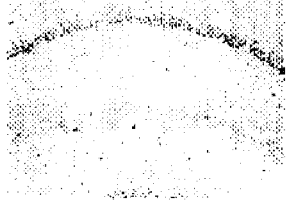
Figure 30E:
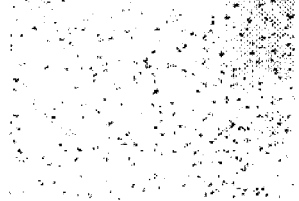
Figure 30F:
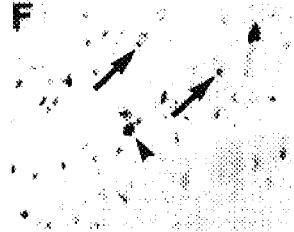
Figure 30G:
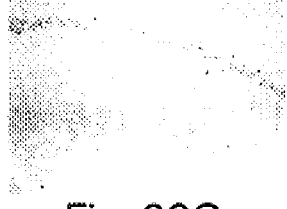
Figure 30H:
Figure 30I:
Figure 31A:
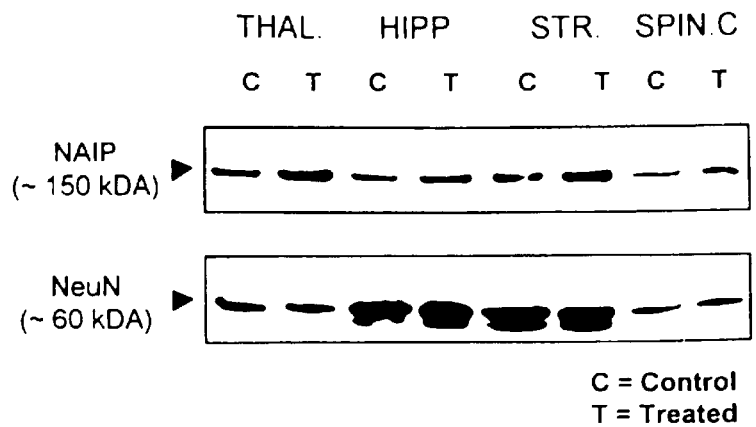
FIGS. 31A–31C are photograph showing the effects of K252a treatment on NAIP levels. A. Effects of a single administration of K252a (0.1 mg/kg, s.c.) on NAIP and NeuN levels in the thalamus, hippocampus, striatum and spinal cord. (A) Western analysis of NAIP levels in the thalamus (THAL.), hippocampus (HIPP.), striatum (STR.) and spinal cord (SPIN. C) 3 h after a single of vehicle (1 ml/kg, s.c.) (control=C) or K252a (0.1 mg/kg, s.c.) (treated= T). K252a elevated NAIP levels (150 kDa) in all four regions with the largest increases occurring in thalamus and striatum. (B) Western analysis of NeuN levels in the thalamus (THAL.), hippocampus (HIPP.), striatum (STR.) and spinal cord (SPIN. C) 3 h after a single of vehicle (1 ml/kg, s.c.) (control=C) or K252a (0.1 mg/kg, s.c.) (treated=T). High levels of NeuN (60 kDa) were present in hippocampus and striatum while lower levels were present in the thalamus and spinal cord. In all four brain regions, NeuN levels were similar in control and treated conditions indicating that each of these lanes was loaded with equivalent amounts of proteins. The same membrane was used for immunoblotting of NAIP and NeuN. B. Comparison of the effects of acute and chronic administration of K252a on NAIP levels in the hippocampus. Western analysis of NAIP levels in the hippocampus after a single injection of vehicle (1 ml/kg, s.c.) or K252a (0.1 mg/kg, s.c.) or chronic administration of K252a (0.1 mg/kg, s.c., once daily for 7 days). By comparison to vehicle injected animals, a single administration of K252a elevated NAIP levels (150 kDa) in all three animals. Chronic administration of K252a produced a further elevation of NAIP levels in each of the three animals that were examined. C. Densitometric measurement of the effects of single and repeated administration of K252a on NAIP levels in the hippocampus. A single administration of K252a (0.1 mg/kg, s.c.) elevated NAIP levels by approximately 50% while chronic administration of K252a (0.1 mg/kg, s.c., once daily for 7 days) increased NAIP levels by approximately 100%. Histograms and bars represent mean and the standard error of the mean for 3 animals. Asterisk, significantly different from vehicle treated animals ($P<0.01$; Newman-Keuls test). Star, significantly different from animals which received an acute injection of vehicle or K252a ($P<0.01$; Newman-Keuls test).

NAIP-LI was enhanced in CA1 neurons 3 hr after a single administration of K252a (0.1 mg/kg, s.c) (FIGS. 30A and 29D). By 24 h, NAIP-LI had returned to preinjection levels in these neurons (FIG. 30G). Similarly, NAIP-LI in the ventral-medial and ventral-lateral regions of the thalamus were elevated 3 h after a single administration of K252a (0.1 mg/kg, s.c.) (FIGS. 32B and 32E). By 24 h, NAIP-LI had returned to normal levels in these thalamic areas (FIG. 30H). NAIP-LI was also increased in striatal neurons 3 h after K252a (0.1 mg/kg, s.c.) and returned to basal levels by 24 h (FIGS. 32C, 32F and 32I). In the striatum, K252a administration appeared to increase NAIP-LI primarily in medium-sized neurons (FIG. 30F). Immunoblotting indicated that the NAIP antibody selectively recognized a single band with a relative molecular mass of 150 kDa which corresponds to the predicted molecular weight for NAIP (FIG. 31A). Consistent with immunohistochemical results indicating the presence of NAIP within a large number of thalamic neurons, Western analysis demonstrated that this anti-apoptotic protein is highly enriched in the thalamus (FIG. 31A). Despite the fact that NAIP expression appears to be restricted to only 1% of striatal neurons (cholinergic interneurons), levels similar to that observed in the thalamus were found in the striatum. Comparatively smaller, but clearly discernable levels of NAIP protein were detected in the hippocampus and spinal cord. In agreement with our immunohistochemical findings, immunoblotting revealed that NAIP levels were elevated in the striatum, hippocampus and thalamus 3 h after a single administration of K252a (0.1 mg/kg, s.c.) (FIG. 31A). As a control for protein loading, Western analysis of NeuN levels was performed on the same membrane used to detect NAIP. Immunoblotting demonstrated that high levels of NeuN (60 kDa) are present in the hippocampus and striatum while lower levels are found in the thalamus and spinal cord (FIG. 31A). In all four brain regions, NeuN levels were similar in vehicle (1 ml/kg, s.c.) and K252a (0.1 mg/kg, s.c.) treated animals confirming that each lane was loaded with equivalent amounts of protein.

Example 7

Effects of Acute K252a Administration on NAIP-I in the Hippocampus, Stratum and Thalamus Two groups, composed of 3 animals each, were injected with K252a (0.1 mg/kg, s.c.) and given an overdose of pentobarbital (100 mg/kg, i.p.) either 3 h or 24 h later. A third group, containing 3 animals, served as vehicle controls. These animals were injected with vehicle (1 mg/kg, s.c.) and given an overdose of pentobarbital (100 mg/kg, i.p.) 3 hr later. All animals were perfused with saline (200 ml) and 4% paraformaldehyde (150 ml) after onset of anaesthesia. The brains were removed, postfixed, cryoprotected and sections 12 μm thick cut through the hippocampus, striatum and thalamus using a cryostat. Sections were processed for NAIP-I.

NAIP-I was enhanced in CA1 neurons 3 hr after a single administration of K252a (0.1 mg/kg, s.c) (FIG. 7). By 24 h, NAIP-I had returned to preinjection levels in these neurons. Similarly, NAIP-I was increased in striatal neurons 3 h after K252a (0.1 mg/kg, s.c.) and returned to basal levels by 24 h. In the striatum, K252a appeared to increase NAIP-I primarily in medium-sized neurons (FIG. 7). K252a (0.1 mg/kg, s.c.) also produced an elevation of NAIP-I in the ventral-medial and ventral-lateral regions of the thalamus (FIG. 7). By 24 h, NAIP-I had returned to normal levels in these thalamic areas.

Example 8

Effects of Acute K252a Administration on NAIP and NeuN in the Hippocampus, Striatum, Thalamus and Spinal Cord Two groups, composed of 3 animals each, were injected with vehicle (1 ml/kg, s.c.) or K252a (0.1 mg/kg, s.c.) and killed 3 h later by decapitation under pentobarbital anaesthesia. The brains were removed and the dorsal hippocampus, striatum, thalamus and spinal cord dissected over ice. NAIP and NeuN were detected in cytosolic protein extracts from these regions by immunoblotting.

Figure 8:
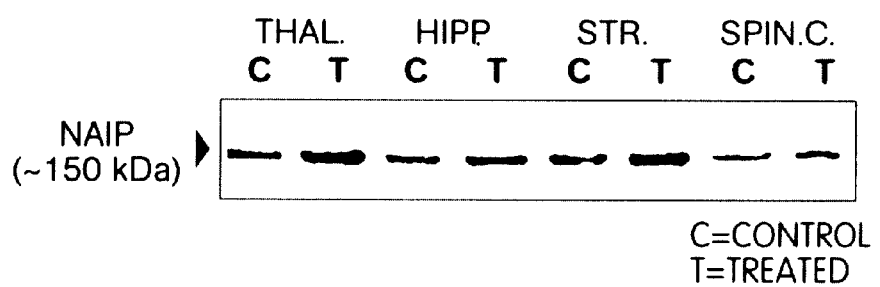
FIG. 8 is a western blot showing analysis of NAIP levels in the thalamus (THAL.), hippocampus (HIPP.), striatum (STR.) and spinal cord (SPIN. C) 3 h after a single of vehicle (1 ml/kg, s.c.) (control=C) or K252a (0.1 mg/kg, s.c.) (treated=T). K252a elevates NAIP levels (150 kDa) in all four regions, with the largest increases occurring in thalamus and striatum.
Figure 9:
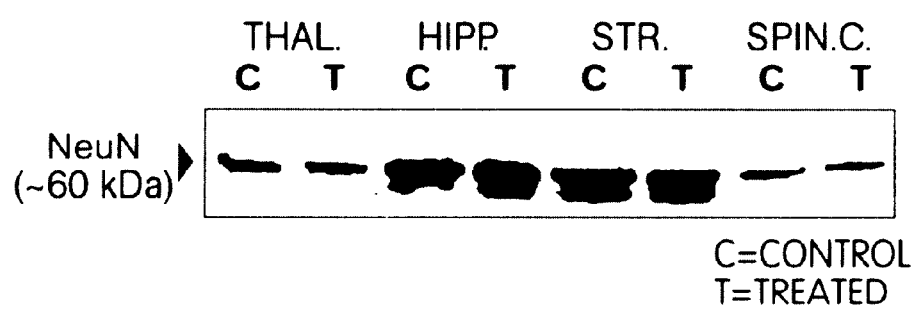
FIG. 9 is a western blot showing analysis of NeuN levels in the thalamus (THAL.), hippocampus (HIPP.), striatum (STR.) and spinal cord (SPIN. C) 3 h after a single of vehicle (1 ml/kg, s.c.) (control=C) or K252a (0.1 mg/kg, s.c.) (treated=T). High levels of NeuN (60 kDa) were present in hippocampus and striatum will lower levels were present in the thalamus and spinal cord. In all four brain regions, NeuN levels were similar in control and treated conditions indicating that each of these lanes was loaded with equivalent amounts of proteins. The same membrane was used for immunoblotting of NAIP and NeuN.

Immunoblotting indicated that the NAIP antibody selectively recognized a single band with a relative molecular mass of 150 kDa. This band corresponds to the predicted molecular weight for NAIP (FIG. 8). Comparison of NAIP levels in the various forebrain regions indicates that NAIP is most abundant in thalamus and striatum. Comparatively smaller, but clearly discernable levels of NAIP protein are detected in the hippocampus and spinal cord. Consistent with the immunohistochemical results, Western analysis reveals that NAIP levels are elevated in the striatum, hippocampus and thalamus 3 h after a single administration of K252a (0.1 mg/kg, s.c.). (As a control for protein loading, Western analysis of NeuN levels was performed on the same membrane used to detect NAIP.) Immunoblotting demonstrates that high levels of NeuN (60 kDa) are present in the hippocampus and striatum while lower levels are found in the thalamus and spinal cord (FIG. 9). In all four brain regions, NeuN levels were similar in vehicle (1 ml/kg, s.c.) and K252a (0.1 mg/kg, s.c.) treated animals indicating that each lane was loaded with equivalent amounts of protein.

Example 9

Effects of Chronic K252a Administration on Ischemia-induced Neuronal Loss in the CA1 Region of the Hippocampus Two groups, composed of 6 animals each, were injected subcutaneously (s.c.) with vehicle (1 ml/kg; aqueous solution containing 10% cyclodextrin and 0.5% DMSO) or K252a (0.1 mg/kg) once daily for 7 days. All of the animals were subjected to 4-VO (10 min) 3 h after the last injection and given a second injection as soon as circulation was restored. A third group, composed of 6 animals, were injected with vehicle as described previously and subjected to sham 4-VO. Animals continued to receive either K252 (0.1 mg/kg, s.c.) or vehicle (1 ml/kg, s.c.) once daily for five days after the 4-VO or sham procedure. All of the animals were given an overdose of pentobarbital (100 mg/kg, s.c) and perfused with saline (200 ml) followed by 4% paraformaldehyde (150 ml) 4 h after the last injection. The brains were removed, post-fixed, cryoprotected and sections 12 µm thick cut through the dorsal hippocampus with a cryostat. Surviving neurons in the CA1 region of the hippocampus were detected using a monoclonal antibody that recognizes the neuron specific marker NeuN (Mullen et al., Development 116:201–211, 1992).

Figure 4A:
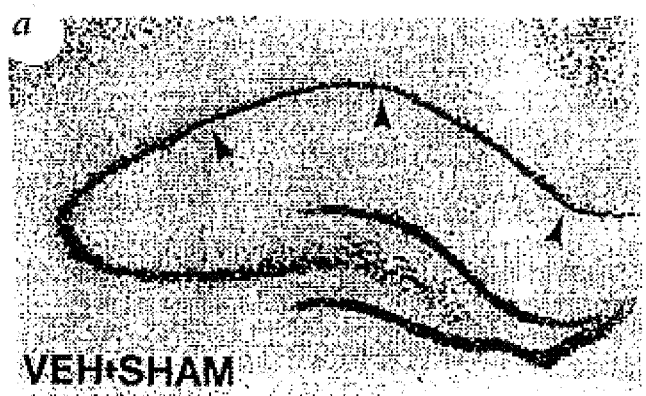
FIGS. 4A–4C are photographs showing the effects of chronic pretreatment with K252a on CA1 neuronal loss 5 days after 10 min of four-vessel occlusion (4-VO). Hippocampal neurons are detected with a monoclonal antibody (A60) against the neuron-specific marker NeuN. (A) NeuN-like immunoreactivity in the CA1 region (arrows) of sham-operated animals injected with vehicle (VEH+SHAM). (B) Massive loss of NeuN-like immunoreactive neurons in the CA1 region (arrows) of vehicle-treated animals 5 days after recirculation (VEH+4-VO). (C) Reduction of ischemia-induced neuronal death in the CA1 region (arrows) after chronic K252a administration (K252a+4-VO). Scale bar= 500 μm.
Figure 4B:
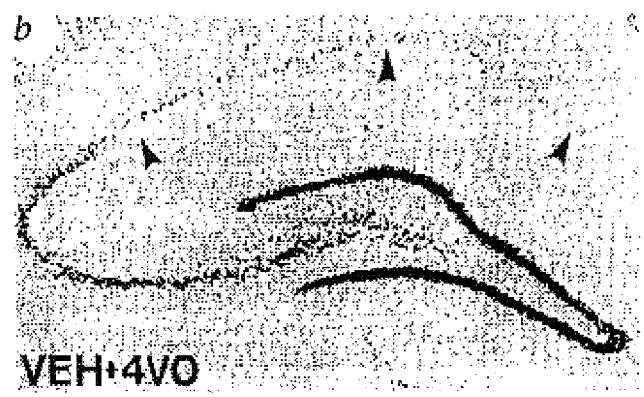
Figure 4C:
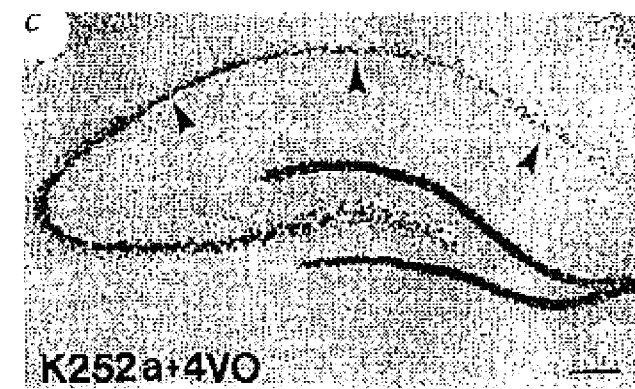
Figure 5:
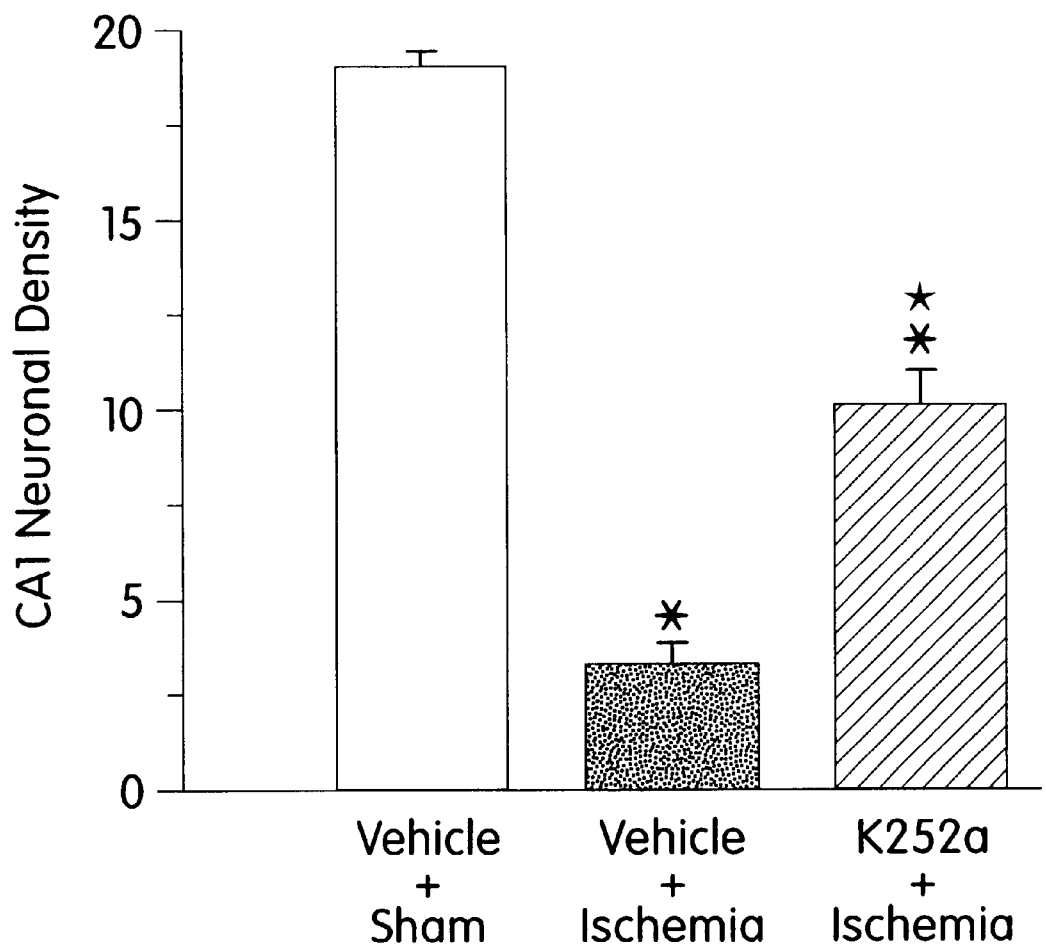
FIG. 5 is a photograph showing the neuroprotective effects of chronic K252a administration on CA1 neurons after transient forebrain ischemia. The density of CA1 neurons expressing NeuN-like immunoreactivity is assessed by computer-assisted image analysis. Neuronal density represents the number of labelled cells per 100 μm length of the CA1 pyramidal layer. Counts are performed on 100 μm lengths of the medial, central and lateral aspects of the CA1 region and averaged. A 70% loss of CA1 neurons is detected in the CA1 region 5 days after 10 min of 4-VO (ISCHEMIA). Subcutaneous injection of K252a (0.1 mg/kg/day) for 7 days prior to 4-VO and each day afterwards (5 days) reduced ischemic damage in the CA1 region by approximately 50% (K252a+ISCHEMIA). Asterisk, significantly different from vehicle-treated shams (VEHICLE+ SHAM) ($p<0.01$). Star, significantly different from vehicle-treated animals subjected to 4-VO (VEHICLE+ISCHEMIA) ($P<0.01$).
Figure 6A:
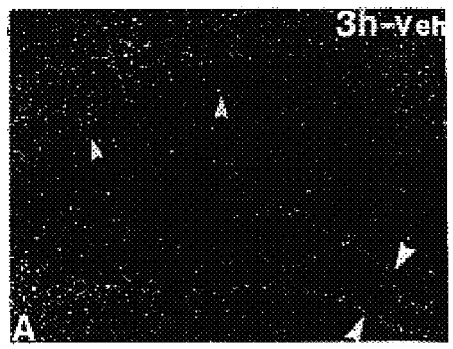
FIGS. 6A–6F are photographs showing the effects of a single administration of vehicle (1 ml/kg, s.c.) (A) or K252a (0.1 mg/kg, s.c) (B–F) on NAIP mRNA levels in the hippocampus as measured by in situ hybridization histochemistry. NAIP mRNA levels are below the limit of detection in hippocampus CA1 neurons (small arrows) and barely detectable in the dentate gyrus (large arrows) 3 h after vehicle (1 ml/kg, s.c.) (A). NAIP mRNA levels are elevated 1.5 h (B) and 3 h (C) following K252a administration in both CA1 (small arrows) and dentate (large arrows) neurons. At 6 h (D), the hybridization signal had returned to normal levels in both the CA1 region and dentate gyrus. NAIP mRNA levels remained at basal levels in the hippocampus 12 h (E) and 24 h (F) after K252a administration. Scale bar=500 μm.
Figure 6B:
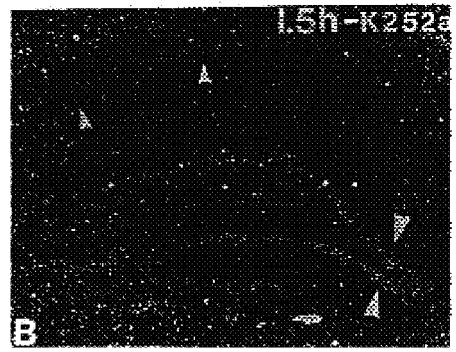
Figure 6C:
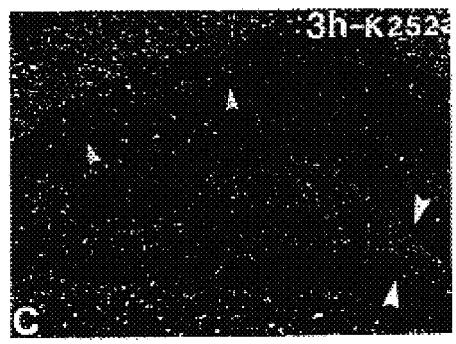
Figure 6D:
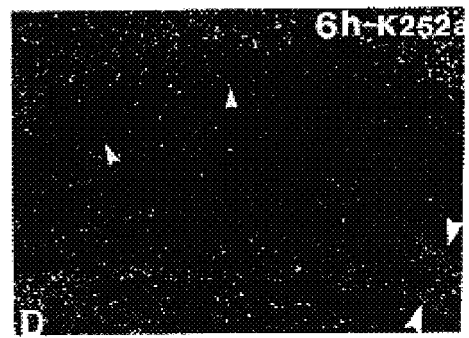
Figure 6E:
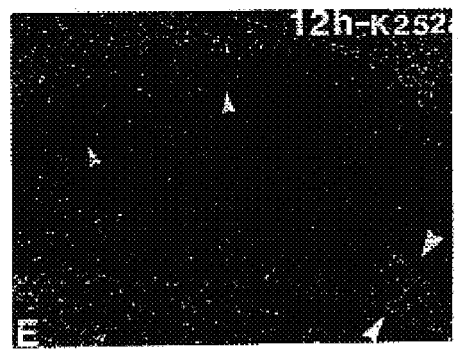
Figure 6F:
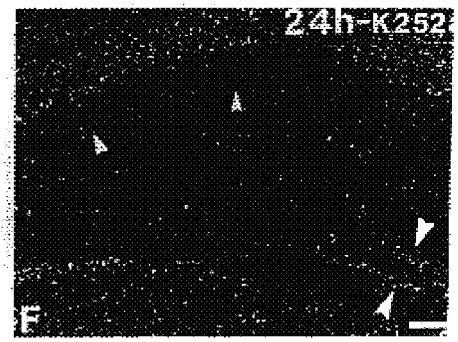
Figure 7A:
FIGS. 7A–7I are photographs showing the effects of a single administration of vehicle (1 ml/kg, s.c.) or K252a (0.1 mg/kg, s.c.) on NAIP-like immunoreactivity in the hippocampus (A, D and G) striatum (B, E and H) and thalamus (C, F and I). In animals treated with vehicle, moderate levels of NAIP-like immunoreactivity are present in hippocampal CA1 (CA1; A) and thalamic (THAL; C) neurons. In striatum, high levels of NAIP-like immunoreactivity are exhibited by cholinergic neurons (large arrow), whereas low levels are detected in medium-sized striatal neurons (small arrow) (B). NAIP-like immunoreactivity was elevated in all three regions 3 h after administration of K252a (0.1 mg/kg, s.c.) (D, E and F). In striatum, K252a appears to elevate NAIP-like immunoreactivity primarily in medium-sized neurons (small arrow) (E). By 24 hours, NAIP-like immunoreactivity had returned to basal levels in the hippocampus (G), striatum (H) and thalamus (I). Scale bar=150 μm.
Figure 7B:
Figure 7C:
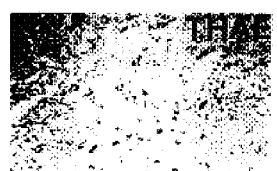
Figure 7D:
Figure 7E:
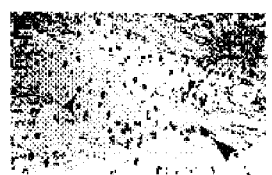
Figure 7F:
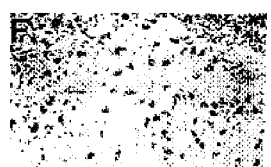
Figure 7G:
Figure 7H:
Figure 7I:

Systemic administration of K252a (0.1 mg/kg, s.c., once daily) for 7 days prior to 4-VO and each day afterwards significantly reduced the loss of hippocampal CA1 neurons produced by 10 minutes of transient forebrain ischemia (FIG. 4). Cell counts performed in the medial, central and lateral thirds of the hippocampus indicated that K252a reduced depletion of CA1 neurons by about 50% (FIG. 5).

Example 10

Effects of Chronic K252a Administration on NAIP Protein Levels

Figure 31B:
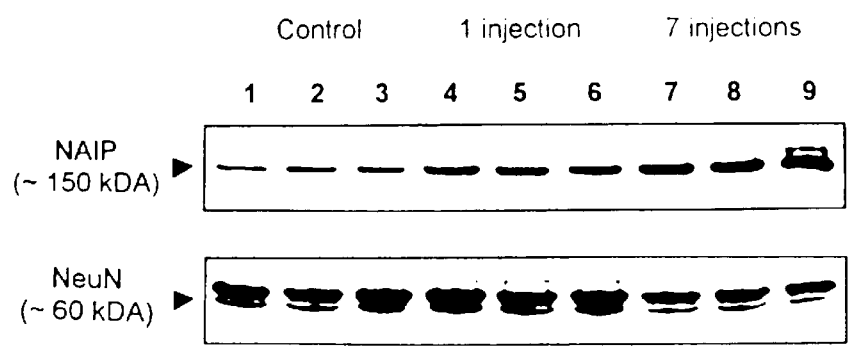
Figure 31C:
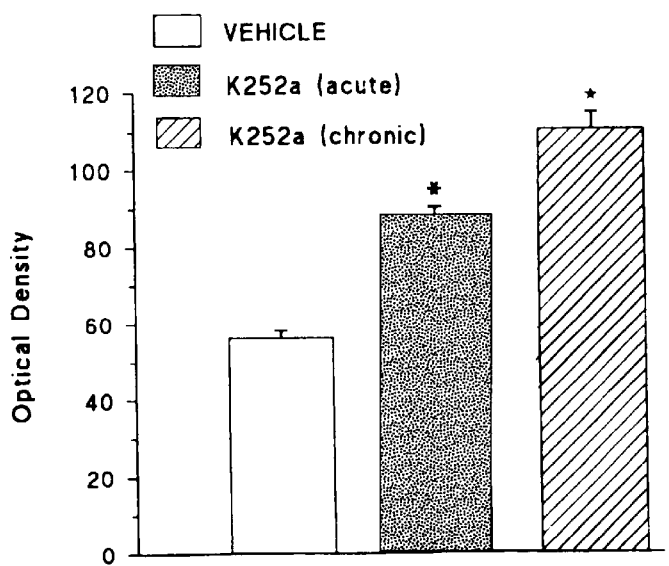

Acute administration of K252a (0.1 mg/kg, s.c.) appeared to elevate NAIP levels in the hippocampi of each of the three animals examined (FIG. 31B). Optical density measurements of the 150 kD NAIP immunoreactive band indicated that acute administration of K252a (0.1 mg/kg, s.c.) elevated NAIP levels in the hippocampus by approximately 50% (FIG. 31C). Levels of NAIP were further elevated by chronic administration of K252a (0.1 mg/kg, s.c., once daily for 7 days) (FIGS. 32B and 32C). By comparison with vehicle injected controls, chronic administration of K252a (0.1 mg/kg, s.c., once daily for 7 days) increased NAIP concentration by approximately 100%. As a control for protein loading, Western analysis of NeuN levels was performed on the same membrane used to detect NAIP. Immunoblotting demonstrated that NeuN levels were not elevated by either acute or chronic administration of K252a indicating that each lane was loaded with equivalent amounts of protein (FIG. 31B).

Example 11

Effects of Acute K252a Administration on Levels of NAIP mRNA in the Hippocampus

Five groups, composed of 3 animals each, were injected with K252a (0.1 mg/kg, s.c) and killed 1.5, 3, 6, 12 or 24 h later by decapitation under pentobarbital anaesthesia. A sixth group, containing 3 animals, was injected with vehicle (1 ml/kg, s.c.) and killed in an identical fashion 3 hours later. The brains were rapidly removed, frozen in isopentane (−65° C.) and sections 12 µm thick cut through the hippocampus using a cryostat. Detection of NAIP mRNA by in situ hybridization histochemistry was performed on the hippocampal sections.

A single administration of K252a (0.1 mg/kg, s.c.) produced an elevation of NAIP expression in the dentate gyrus and CA1 neurons at 1.5 to 3 hr (FIG. 6). By 6 h, NAIP mRNA levels appeared to have returned to basal levels in these regions. NAIP levels remained at basal levels 12 h and 24 h after injection of K252a (0.1 mg/kg, s.c.).

Example 12

Effects of K252a Administration on NAIP Expression

Figure 32A:
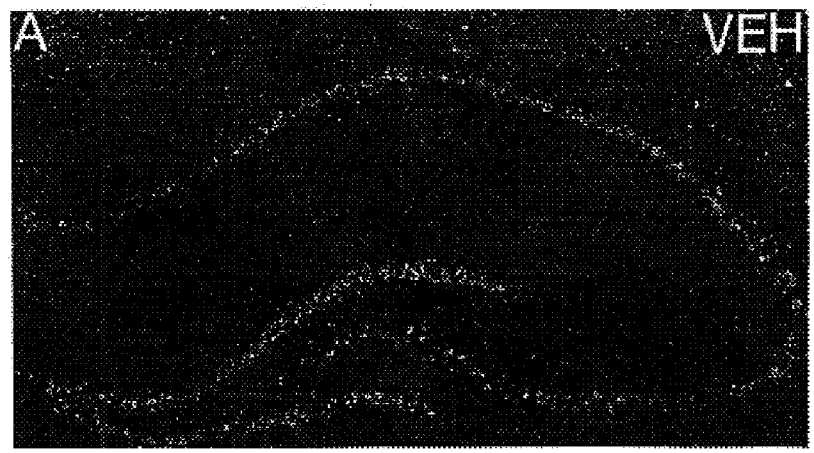
FIGS. 32A–32C are photographs showing the effects of acute and chronic administration of K252a on expression of NAIP mRNA in the hippocampus as detected by in situ hybridization histochemistry. Low levels of NAIP mRNA were present in the hippocampus of animals injected with vehicle (1 ml/kg, s.c.) (A). A single administration of K252a (0.1 mg/kg, s.c.) elevated NAIP mRNA levels in hippocampus (B). Chronic administration of K252a (0.1 mg/kg, s.c., once daily for 7 days) produced a further elevation of NAIP mRNA levels (C). All animals were sacrificed 3 h after the last injection.
Figure 32B:
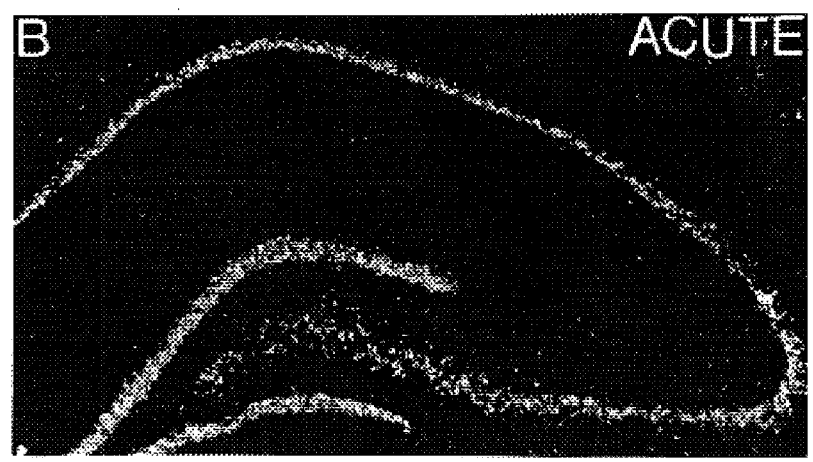
Figure 32C:
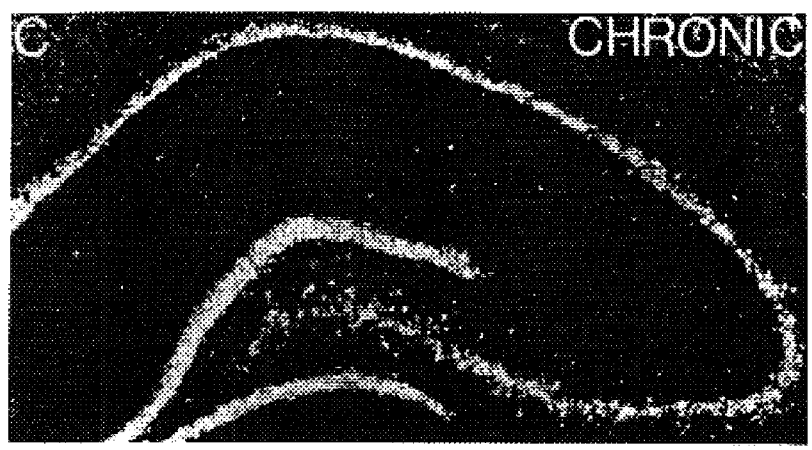

In situ hybridization histochemistry revealed that low levels of NAIP mRNA are present in the hippocampus of animals injected with vehicle (FIG. 32A). Administration of K252a (0.1 mg/kg, s.c.) produced a rapid elevation of NAIP mRNA levels in CA1–CA4 subfields as well as the dentate gyrus (FIG. 32B). Chronic administration of K252a (0.1 mg/kg/day for 7 days) appeared to result in a further elevation of NAIP mRNA levels in the hippocampus (FIG. 32C).

Example 13

Chronic K252a Administration Protects Neurons From Ischemic Injury

Figure 33A:
FIGS. 33A–33D are photographs showing the effects of chronic pretreatment with K252a on CA1 neuronal loss 5 days after 10 min of four-vessel occlusion (4-VO). A. Immunohistochemical detection of neurons with a monoclonal antibody (A60) against the neuron-specific marker NeuN in the hippocampus of sham-operated animals injected with vehicle (VEH+SHAM, arrows indicate CA1 region). B. Massive loss of NeuN-like immunoreactive neurons in the CA1 region (arrow heads) of vehicle-treated animals 5 days after recirculation (VEH+4-VO). C. Reduction of ischemia-induced neuronal death in the CA1 region (arrow heads) after chronic K252a administration (K252a+4-VO). Scale bar=500 µm. D. The density of CA1 neurons expressing NeuN-like immunoreactivity assessed by computer-assisted image analysis. A 70% loss of CA1 neurons was detected in the CA1 region 5 days after 10 min of 4-VO (ISCHEMIA). Chronic administration of K252a reduced ischemic damage in the CA1 region by approximately 50% (K252a+ISCHEMIA). Histograms and bars represents mean and the standard error of the mean for 6 animals. Asterisk, significantly different from vehicle-treated shams (VEHICLE+SHAM) ($P<0.01$; Newman-Keuls test). Star, significantly different from vehicle-treated animals subjected to 4-VO (VEHICLE+ISCHEMIA) ($P<0.01$; Newman-Keuls test).
Figure 33B:
Figure 33C:
Figure 33D:
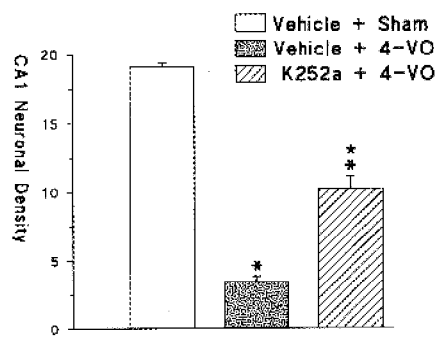

Transient cerebral ischemia produced by 10 min of 4-VO reduced the number of CA1 neurons in the hippocampus by approximately 70% (FIGS. 33A and 33B). Systemic administration of K252a (0.1 mg/kg, s.c.; once daily) for 7 days prior to 4-VO and each day afterwards (5 days) significantly reduced the loss of hippocampal CA1 neurons produced by 10 minutes of transient forebrain ischemia (FIG. 33C). Cell counts indicated that chronic K252a administration reduced depletion of CA1 neurons by about 50% (FIG. 33D).

Example 14

Effects of K252a on Blood Pressure, pH, $pO_2$ and $pCO_2$

The basal values (mean±standard error of the mean) for blood pressure, pH, $pO_2$ and $pCO_2$ were 114.5±13.8 mm Hg, 7.44±0.01, 92.2±3.1 mm Hg and 35.6±4.9 mm Hg, respectively. These values were not significantly different from those measured at each of the time points examined after administration of K252a (0.1 mg/kg, s.c.).

Example 15

Post-ischemia Neuroprotective Effects of Virally-mediated NAIP Overexpression

Stereotaxic injection of a recombinant adenoviral construct (pAdex1CAwt) containing the bacterial enzyme lacZ into the contralateral hippocampus did not reduce the loss of CA1 neurons 5 days after an episode of transient forebrain ischemia (FIG. 34A). In contrast, injection of the adenoviral construct containing myc-tagged NAIP into the dorsal hippocampus significantly reduced the loss of CA1 neurons (FIG. 34B). Cell counts demonstrated that by comparison to the lacZ injected side, CA1 loss in the hippocampus injected with the NAIP adenovirus was reduced by approximately 60% (FIG. 34E). Myc immunoreactivity and X-gal staining confirmed that hippocampal neurons were infected by the adenovirus constructs containing myc-tagged NAIP or lacZ, respectively (FIGS. 34C, 34D). Cell counts of Myc-(7±1) and X-gal-(10±2) stained neurons revealed that similar numbers of neurons were labelled by these two adenoviral constructs (P>0.05). However, within hippocampi injected with the NAIP adenovirus, significantly more CA1 neurons were protected from ischemic injury (15±2) than displayed Myc immunoreactivity (7±1) (P<0.01).

Example 16

NAIP and IAP Upregulation in Kindled Rats

We have looked at the effect of kindling on naip and lap gene expression and protein levels using in situ and immunocytochemistry techniques. Our results indicate that the NAIP gene, and at least one IAP gene, XIAP, are upregulated in the brains of kindled rats. More importantly this upregulation is observed in those brain regions that prove to be resistant to the excessive excitation occurring during SE.

From this observation, we make two important conclusions. First, NAIP and IAP gene expression may be induced using this physiological mechanism. Second, those factors which are known to be present at increased levels after kindling, e.g., BDNF and NGF, may be used to increase IAP and NAIP levels both in the neuronal context and in other contexts where increased NAIP or IAP expression is desirable.

Example 17

Transgenic Therapy Using a NAIP Viral Vector

We have stereotaxically administered a human replicative-deficient adenoviral construct (pAdex1CAwt; Liston et al., Nature 379:349, 1996) containing the NAIP gene sequence into the dorsal hippocampus of male Wistar rats. Animals are then subjected to transient forebrain ischemia in order to determine if the adenovirus injection has rendered the hippocampus more resistant to ischemic cell death.

Under pentobarbital (50 mg/kg, i.p.) anaesthesia, 3 $\mu$l of adenoviral suspension containing approximately $1\times10^9$ particles ml$^{-1}$ is injected into the CA1 region of the right hippocampus using a sterile Hamilton syringe (5 $\mu$l) at a rate of 0.5 $\mu$l min$^{-1}$. The needle is then slowly removed over a 2 min. period and the wound closed with sutures. A control injection (3 $\mu$l of LacZ adenovirus construct suspended in 20% sucrose in 0.01 M phosphate buffered saline) is made into the CA1 region of the left hippocampus. One week after sterotaxic surgery, animals are subjected to transient global ischemia. Transient global ischemia (10 min) is performed using the four-vessel occlusion technique previously described in PM-117. Five days after four-vessel occlusion, all of the animals are killed with an overdose of pentobarbital (100 mg/kg, i.p.). Half of the animals are perfused transcardially with 4% paraformaldehyde. The brains are then removed, cryoprotected in 10% sucrose and sectioned on a cryostat. The remaining half are decapitated and the brains rapidly frozen in isopentane cooled to −65° C. with dry ice. Fresh frozen sections are cut from this tissue using a cryostat. Alterations in NAIP mRNA and protein are assessed by performing in situ hybridization histochemistry on fresh frozen sections and immunohistochemistry on paraformaldehyde-fixed tissue, respectively.

Figure 10:
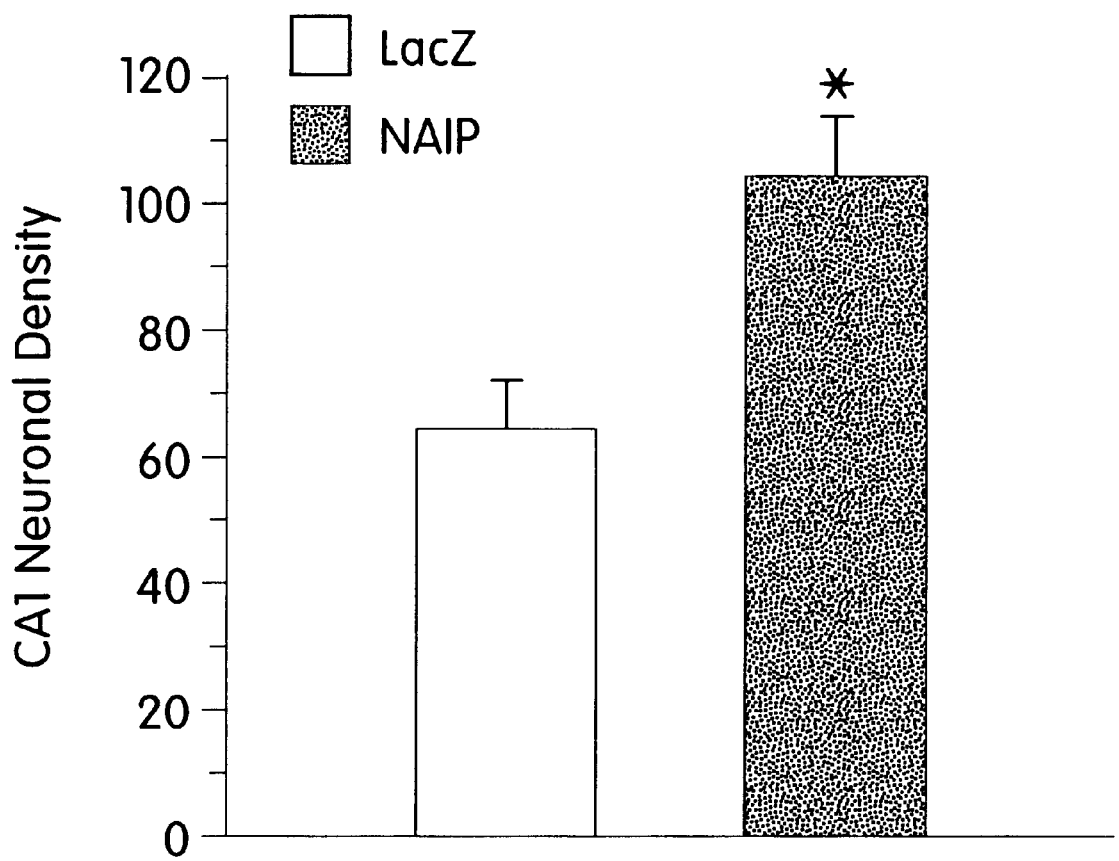
FIG. 10 is a graph showing neuronal density in cells expressing the NAIP transgene following transient ischemia.

FIG. 10 shows the increased prevention of cell death following ischemia in animals treated with a NAIP expressing transgene. CA1 neurons labelled with the NeuN antibody were counted using an image analysis system. Cell counts revealed that, compared to the LacZ injected side, the NAIP construct reduced CA1 neuronal death by about 40%. The asterisk denotes a significant difference between animals treated with a NAIP expressing transgene and animals treated with a LacZ expressing transgene, p<0.05.

Example 18

Axotomy Elevates NAIP and XIAP Expression Facial Motoneurons

Figure 26A:
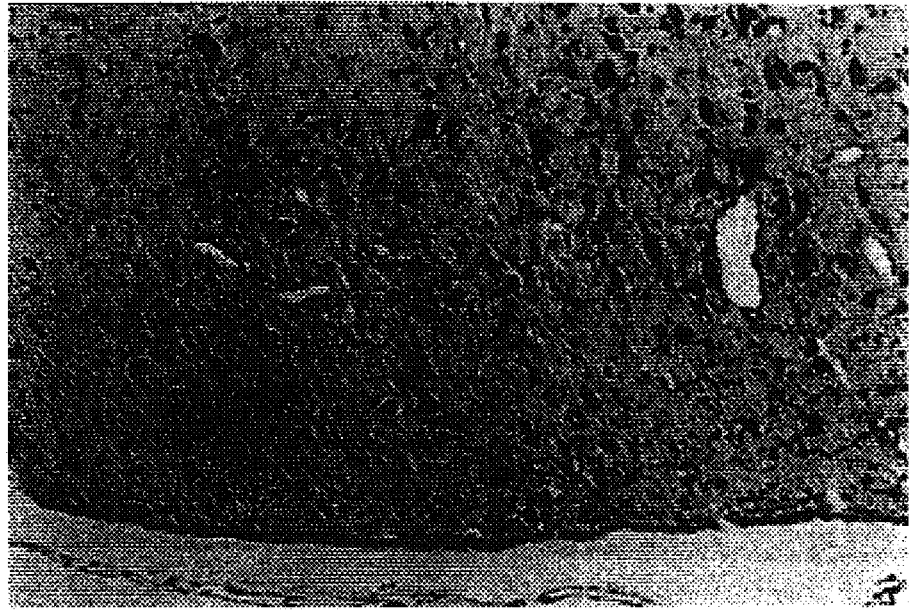
FIGS. 26A–26B are photographs showing neurons which are axotomized (top) and a control.
Figure 26B:

It is well established that motoneurons of adult mammals survive axonal injury while those in newborns die within 2–7 days (FIG. 26). The mechanism of death appears to be apoptotic in nature. We therefore tested the hypothesis that members of the IAP family mediate the survival of adult motoneurons and that this protective mechanism is not seen in the newborn. Consequently, we have compared the effects of axotomy on NAIP, XIAP and HIAP-2 expression in facial motoneurons of adult and newborn rats.

Figure 27:
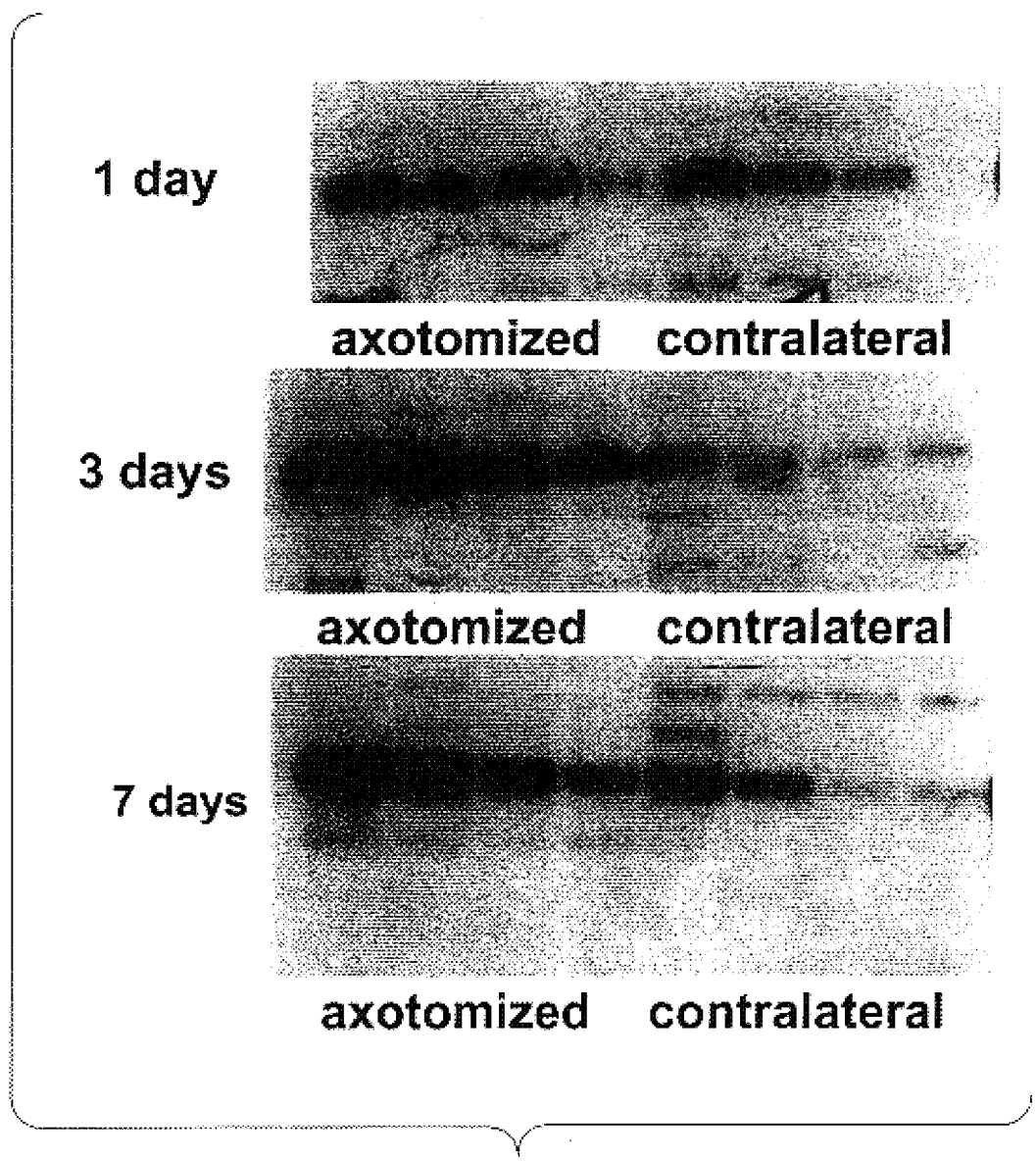
FIG. 27 is a photograph showing NAIP levels in axotomized cells and controls after 1, 3, and 7 days.
Figure 28A:
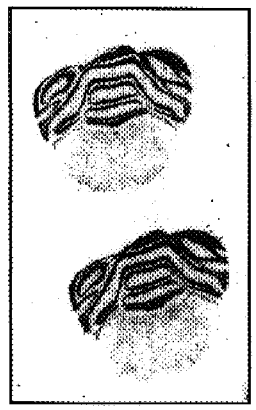
FIGS. 28A–28C are photographs showing IAP expression after facial axotomy.
Figure 28B:
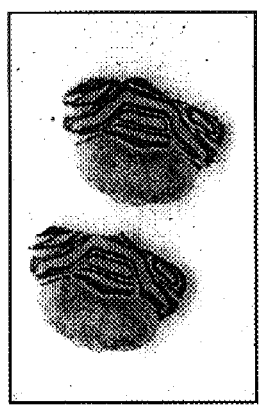
Figure 28C:
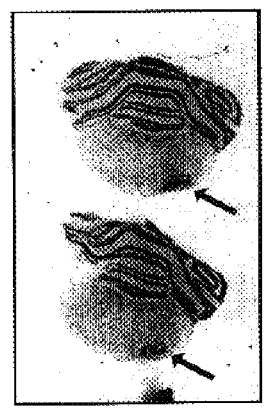

At day 1, expression of NAIP mRNA was increased by 1.5–2 fold in the axotomized facial nucleus of the adult rat (FIG. 27). On day 3, the axotomized side displayed a 8–10 fold increase as assessed by quantification of the serial dilution series. This increase was maintained throughout the experimental period, i.e. days 7–14. Amplifications using primers for XIAP revealed only a minor increase after axotomy (data not shown). In situ hybridization histochemistry revealed that NAIP, and to a lesser extent XIAP, expression were elevated 3 days after axotomy in adult rats (FIG. 28). In contrast to adults, newborn facial nuclei failed to show a comparable increase in NAIP after axotomy (FIG. 29).

These data indicate that NAIP and XIAP may play a role in the survival of adult motoneurons after axonal injury. They also suggest that the death observed in the newborn may be related to the absence of an increase in NAIP expression. Functional testing of this hypothesis in currently under way using NAIP expression vectors.

NAIP and possibly other members of the IAP family are involved in the survival response of injured motoneurons. This provides further support for the proposal that stimulation of NAIP expression is a viable therapeutic approach for the promotion of motoneuron survival.

What is claimed is:

1. A method for enhancing survival of a neuron in vitro, said method comprising introducing a nucleic acid molecule encoding a protein selected from the group consisting of a neuronal apoptosis inhibitory protein (NAIP) and an inhibitor of apoptosis protein (IAP), said introducing being sufficient to produce an increase in the likelihood of said neuron surviving relative to an untreated control.

2. The method of claim 1, wherein said protein is NAIP.

3. The method of claim 1, wherein said IAP is selected from the group consisting of human IAP1 (HIAP1), human IAP2 (HIAP2), and X-linked IAP (XIAP).

4. The method of claim 1, wherein said neuron is a neuron from an individual having a neurodegenerative disease.

5. The method of claim 4, wherein said neurodegenerative disease is Parkinson's Disease.

6. The method of claim 1, wherein said increase in the likelihood of said neuron surviving is by at least 20%.

7. The method of claim 1, wherein said neuron is a neuron selected from the group consisting of hippocampal neurons, dopaminergic neurons of the midbrain, retinal ganglion neurons, neurons having experienced traumatic injury, and basal forebrain cholinergic neurons.

8. The method of claim 1, wherein said introducing is by administering a transgene encoding a NAIP or an IAP polypeptide in an expressible genetic construct.

9. The method of claim 8, wherein said expressible genetic construct includes a constitutive promotor.

10. The method of claim 9, wherein said promotor is an enolase promotor or a neurofilament promotor.

11. The method of claim 8, wherein said expressible genetic construct includes a regulatable promotor.

12. The method of claim 8, wherein said transgene is within a viral vector.

13. The method of claim 12, wherein said viral vector is an adenovirus vector, a herpes virus vector, or a polio virus vector.

14. The method of claim 8, wherein said administering is to a cell isolated from a patient diagnosed as having a predisposition to ischemic events.

15. The method of claim 8, wherein said IAP is selected from the group consisting of HIAP1, HIAP2, and XIAP.

16. The method of claim 3, wherein said HIAP1 is human HIAP1.

17. The method of claim 3, wherein said HIAP2 is human HIAP2.

18. The method of claim 3, wherein said XIAP is human XIAP.

19. The method of claim 1, wherein said neuron is selected from the group consisting of hippocampal neurons, dopaminergic neurons of the midbrain, retinal ganglion neurons, and basal forebrain cholinergic neurons and said introducing is by administering a transgene encoding a NAIP or an IAP polypeptide in an expressible genetic construct.

* * * * *